(12) United States Patent
Li et al.

(10) Patent No.: US 10,753,900 B2
(45) Date of Patent: Aug. 25, 2020

(54) REAL-TIME IN SITU SENSING OF WATER-RELATED PARAMETERS USING MICRO-ELECTRODE ARRAY

(71) Applicant: University of Connecticut, Farmington, CT (US)

(72) Inventors: Baikun Li, South Windsor, CT (US); Yu Lei, Mansfield Center, CT (US); Zhiheng Xu, Farmington, CT (US)

(73) Assignee: University of Connecticut, Farmington, CT (US)

( * ) Notice: Subject to any disclaimer, the term of this patent is extended or adjusted under 35 U.S.C. 154(b) by 84 days.

(21) Appl. No.: 15/639,852

(22) Filed: Jun. 30, 2017

(65) Prior Publication Data
US 2018/0003668 A1    Jan. 4, 2018

Related U.S. Application Data

(60) Provisional application No. 62/356,932, filed on Jun. 30, 2016.

(51) Int. Cl.
| | | |
|---|---|---|
| *G01N 27/403* | (2006.01) | |
| *G01N 27/06* | (2006.01) | |
| *G01N 27/12* | (2006.01) | |
| *G01N 33/18* | (2006.01) | |

(Continued)

(52) U.S. Cl.
CPC ........... *G01N 27/403* (2013.01); *G01N 27/06* (2013.01); *G01N 27/128* (2013.01); *G01N 33/1886* (2013.01); *C02F 2209/02* (2013.01); *C02F 2209/05* (2013.01); *C02F 2209/06* (2013.01);

(Continued)

(58) Field of Classification Search
None
See application file for complete search history.

(56) References Cited

U.S. PATENT DOCUMENTS

| | | | |
|---|---|---|---|
| 3,710,237 A | * | 1/1973 | Watson ................. G01N 27/07 324/446 |
| 4,816,131 A | | 3/1989 | Bomsztyk |
| 5,676,820 A | | 10/1997 | Wang et al. |

(Continued)

OTHER PUBLICATIONS

U.S. Appl. No. 62/356,032, filed Jun. 30, 2016.

*Primary Examiner* — Richard C Gurtowski
(74) *Attorney, Agent, or Firm* — McCarter & English, LLP

(57) ABSTRACT

Improved sensor assemblies are provided. More particularly, the present disclosure provides microelectrode array ("MEA") real-time in situ global sensing assemblies for enhancing efficiency and stability of wastewater treatment systems. In general, the present disclosure provides for a novel global sensing technology utilizing a microelectrode array (MEA) to solve various problems of monitoring wastewater treatment systems. The present disclosure provides for improved systems/methods for monitoring wastewater treatment systems, with the improved systems/methods obtaining a substantially complete global profile of multiple parameters simultaneously. More particularly, the present disclosure provides that by patterning multiple electrodes (e.g., mm-sized electrodes) on a film (e.g., thin plastic film), a MEA can monitor multiple parameters simultaneously in 2-dimension (2-D) of a given system so that global dynamic stratification inside such systems can be real-time visualized for swift response under various wastewater conditions.

9 Claims, 23 Drawing Sheets

(51) Int. Cl.
 *G01N 27/07* (2006.01)
 *G01N 27/27* (2006.01)
(52) U.S. Cl.
 CPC .......... *C02F 2209/22* (2013.01); *G01N 27/07* (2013.01); *G01N 27/27* (2013.01)

(56) References Cited

U.S. PATENT DOCUMENTS

| | | |
|---|---|---|
| 8,182,663 B2 | 5/2012 | Collier et al. |
| 8,202,408 B2 | 6/2012 | Carson et al. |
| 8,414,750 B2 | 4/2013 | Heller et al. |
| 8,901,913 B2 | 12/2014 | Zhu et al. |
| 8,940,142 B2 | 1/2015 | Karhanek et al. |
| 8,965,478 B2 | 2/2015 | Liu |
| 2004/0163954 A1 | 8/2004 | Gurry et al. |
| 2010/0204695 A1* | 8/2010 | Mehta .............. A61B 18/1206 606/42 |
| 2013/0087456 A1* | 4/2013 | Pratt .................. G01N 27/4163 204/406 |

* cited by examiner

Inkjet Print on a plastic film to obtain a whole set MEA array (size:6cm x 30cm) hosting 12 rows of mm-sized 6 types electrodes (72 MEA sensors in total).

(Calibration of dissolved oxygen (DO) MEA sensor)

(Calibration of chloride (Cl) MEA sensor)

FIG. 9B (Lab-tests demo)

FIG. 9A (6-type MEA sensors integrated on a film)

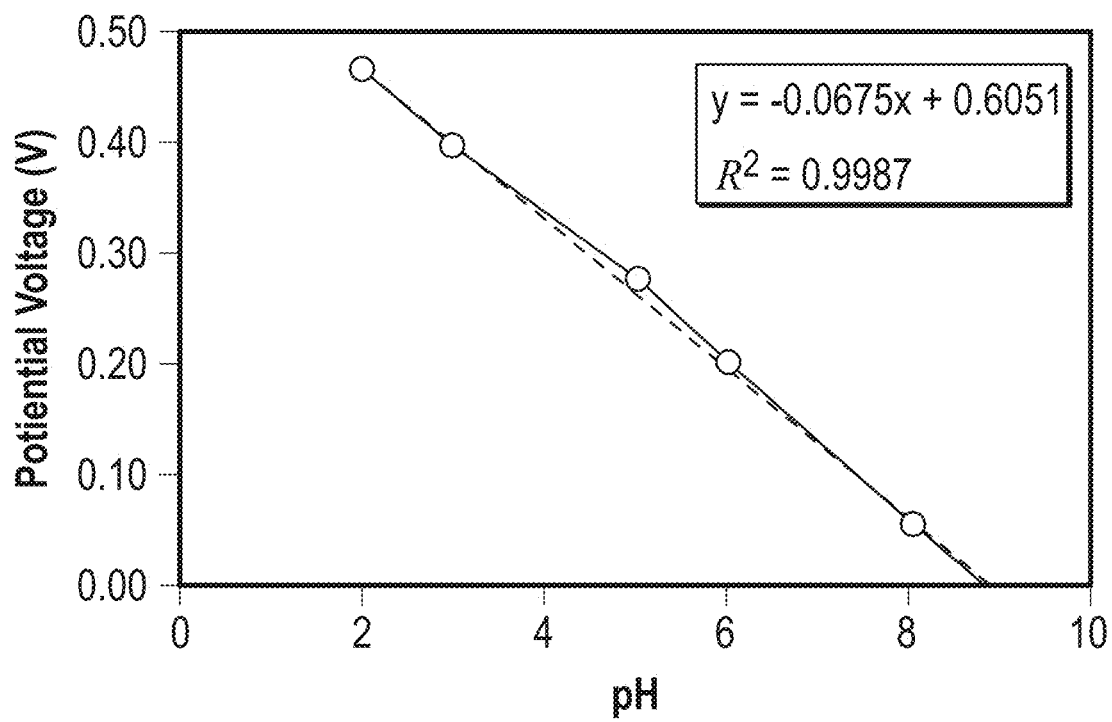
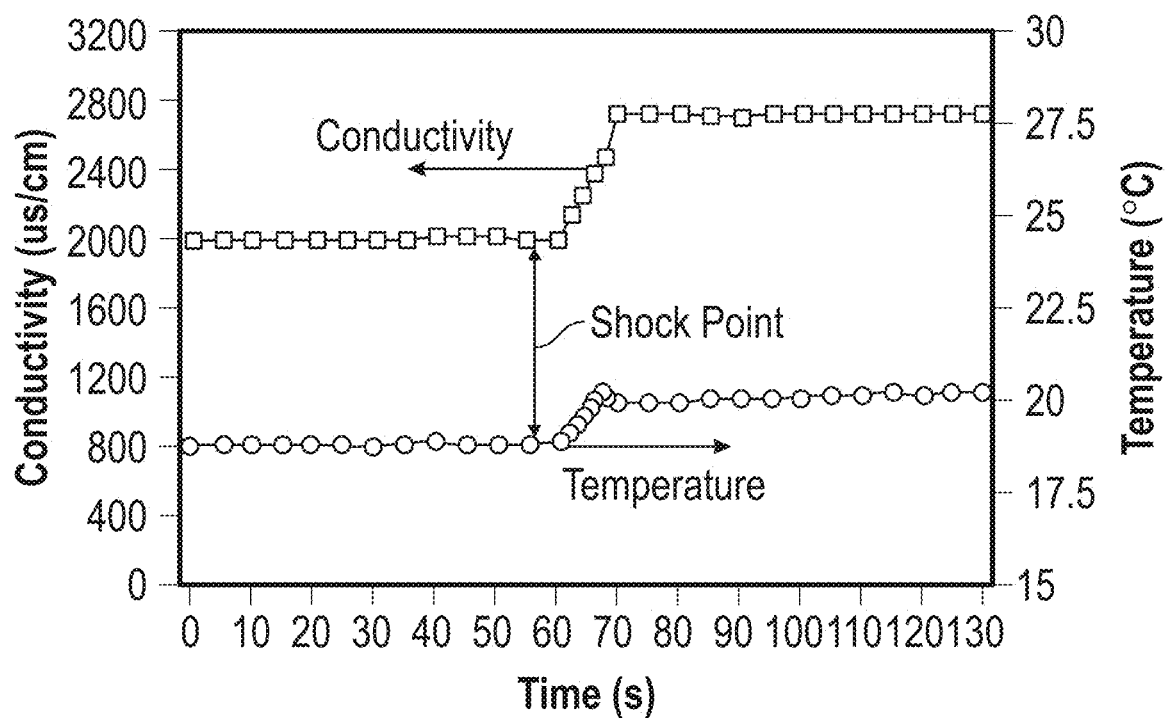
FIG. 11A

(MEA response to Cl⁻ shocks)

(MEA response to salt (NaCl) shocks, and comparted with commercial conductivity sensors, showing high sensitivity and fast response time)

| Concentration (mg/L) | Conductivity of Solution (µs/cm) by Commercial Sensor | 1/R (ohm) by MEA |
|---|---|---|
| 2 | 4.42 | 2.21E-06 |
| 10 | 22.3 | 1.12E-05 |
| 40 | 74.2 | 3.68E-05 |
| 80 | 187 | 9.71E-05 |
| 130 | 256 | 1.23E-04 |
| 180 | 288 | 1.36E-04 |
| 240 | 520 | 2.61E-04 |
| 290 | 610 | 3.06E-04 |
| 400 | 721 | 3.62E-04 |
| 550 | 953 | 4.79E-04 |
| 750 | 1684 | 8.26E-04 |
| 1000 | 1982 | 9.84E-04 |
| 1500 | 2845 | 1.40E-03 |
| 2200 | 3980 | 1.99E-03 |
| 2700 | 5320 | 2.72E-03 |
| 3400 | 6156 | 3.07E-03 |
| 4900 | 8780 | 4.38E-03 |
| 7400 | 13858 | 6.37E-03 |
| 10000 | 17792 | 8.85E-03 |

REAL-TIME IN SITU SENSING OF WATER-RELATED PARAMETERS USING MICRO-ELECTRODE ARRAY

CROSS-REFERENCE TO RELATED APPLICATION

The present application claims priority benefit to a provisional application entitled "Microelectrode Array Real-Time In Situ Global Sensing Device for Enhancing Efficiency and Stability of Wastewater Treatment Systems," which was filed on Jun. 30, 2016, and assigned Ser. No. 62/356,032. The entire content of the foregoing provisional application is incorporated herein by reference.

GOVERNMENT RIGHTS

This invention was made with government support under Project No. 1336425 of the Environmental Engineering Program awarded by the National Science Foundation. The government has certain rights in the invention.

FIELD OF THE DISCLOSURE

The present disclosure relates to sensor assemblies and, more particularly, to microelectrode array ("MEA") real-time in situ assemblies for sensing multiple water/fluid parameters, including assemblies that enhance efficiency and stability of wastewater treatment systems. The disclosed MEA assemblies may be fabricated using inkjet-printing technology.

BACKGROUND OF THE DISCLOSURE

Fundamental physical and chemical parameters reflect the operational status of diverse water/wastewater treatment processes including aerobic/anaerobic systems, coagulation/flocculation units and disinfection contact tanks. A holistic understanding of heterogeneity inside a given system is critical to optimize and troubleshoot operation under dynamic changing conditions. However, traditional sensors can only measure a single parameter at a single sampling point, and fail to profile the complete picture of operational status. Currently, wastewater treatment systems (e.g., aeration tanks, anaerobic digestors, anoxic tanks, storage tanks, pipelines) typically use conventional single-point sensing technology, which generally can only measure one parameter at a sampling site. This type of sensing generally can only obtain local information at a single point of wastewater treatment systems, which inhibits swift and efficient action under various upcoming events (e.g., wastewater quality/quantity, shocks) and can lead to low efficiency and malfunction of systems. In general, conventional probes/electrodes can only measure a single parameter at a single point, so that a broad spectrum of probes have to be installed in a waste facility (e.g., anaerobic digestor or "AD" system) to determine operational status, which can be extremely costly.

Although multi-meters (e.g., YSI® multi-meters) have been commercialized for measuring multiple parameters simultaneously, they are made by packing several probes in a single cartridge, meaning that they can only obtain readings at a single sampling point, and require a large space (FIGS. 1A and 1B). While multi-parameter meters (e.g., multiple probes packed into a single rigid cartridge) have improved monitoring, the single point limitations associated with the meters make it impossible to monitor dynamic waste streams in a heterogeneous system. In addition, multi-parameter meters are costly and generally have large space requirements. For example, a conventional cartridge hosting three (3) probes (e.g. temperature, pH, oxygen) is 1.5 m long and 0.5 m diameter for a permanent installation model, with a cost of S25,000-550,000 [Robert A. Linsenmeier and M. Yancey Charles, Improved fabrication of double-barreled recessed cathode $O_2$ microelectrodes, Journal of applied physiology 63.6 (1987): 2554-2557]. For a system requiring the profile of multiple parameters at high temporal and spatial resolution, numerous multi-parameter meters are needed (e.g. 200-500 probes) with prohibitively high cost and space.

Micro-scale glass pipette electrodes have been developed to measure the chemical profiles inside biofilms and activated sludge flocs. These needle-shaped micro-electrodes are generally fabricated by either shielding a tapered metal wire with a glass micropipette or filling a glass micropipette with a low melting point alloy (e.g., platinum). However, the fragile glass pipette structure, time-consuming fabrication, and need for bulky micromanipulator to position microelectrodes poses severe problems for field applications. Until now, glass pipette micro-electrodes have only been used in well-controlled lab-scale systems.

In the last decade, a micro-fabrication method—photolithography with chemical vapor deposition (PCVD) was developed for fabricating durable micro-scale electrical sensors to monitor water quality (e.g., metals, cyanide and formic acid). But PCVD process is complicated due to high temperature metal vapor (e.g., gold, platinum, etc.) deposition, photomask preparation, photoresist and etching. The strict fabrication condition (e.g., high temperature, dust-free and yellow filter requirement) limits selection of rigid sensor materials (e.g., silicon, silicon oxide) that is difficult for direct deployment in water/wastewater treatment systems. In addition, high cost photomask and metal deposition in PCVD protocols severely limits mass production of diverse types of electrical sensors.

A new fabrication method—inkjet printing technology (IPT) has gained high levels of interest due to three breakthroughs over PCVD. First, the IPT process only involves two steps: substrate material preparation and inkjet printer setup, which is much easier than PCVD process needing over 10 steps. Second, the IPT process can be easily conducted at room temperature and pressure, and thus greatly broadens the selection of sensor substrate materials (e.g., flexible thin polyimide film) that can be easily deployed in water/wastewater systems. Third, the cost of a sensor fabricated using the IPT process is only $0.20 (mainly the ink cost), about $1/150$ of the cost using PCVD, which makes mass fabrication of miniature sensors feasible. IPT has been used to fabricate sensors for detecting hydrogen sulfide and humidity in the air and identifying cancer biomarker protein. However, there has been no report regarding IPT-fabricated sensors for water quality monitoring.

Thus, a need exists for improved sensor assemblies, and related methods of use. These and other inefficiencies and opportunities for improvement are addressed and/or overcome by the assemblies, systems and methods of the present disclosure.

SUMMARY OF THE DISCLOSURE

Conventional water and wastewater treatment processes have been monitored using expensive and inefficient "single-point" probes that can only measure single parameter at single point without obtaining a complete picture of physicochemical or biochemical status. The present disclosure provides advantageous micro-electrode array (MEA) sensors using ink-jet printing technology (IPT). Accordingly to exemplary embodiments of the present disclosure, multiple mm-sized electrodes are printed on a flexible film for simultaneous monitoring of multiple parameters at high temporal and spatial resolution. Indeed, calibration of four types of MEA sensors (temperature, conductivity, dissolved oxygen (DO) and pH) in water solution according to the present disclosure show high coefficient of determination ($R^2 > 0.99$) between the MEA readings and the parameter targeted. Exemplary shock tests have demonstrated high accuracy of MEA sensors and rapid response with a reading frequency of 0.1 second, which captured the shock impacts in more details than commercial probes.

In addition, patterning multiple types of MEA sensors on a single film according to the present disclosure enables auto-correction between targeted parameters and reduces potential measurement errors. Exemplary MEA surface property observations during 4-week immersion in wastewater and waste sludge revealed an intact structure and high mechanic stability. Thus, the systems and methods of the present disclosure provide numerous advantages over existing "single-point" probes, e.g., compact sensor configuration, multiple-parameter monitoring in a single measurement, easy fabrication and ultra-low cost (e.g., \$0.20/sensor), which will decode the system "black box", provide a complete dataset for switch control strategy, and enhance treatment performance at low capital and operational cost.

Accordingly, the present disclosure provides improved sensor assemblies. More particularly, the present disclosure provides microelectrode array ("MEA") real-time in situ global sensing assemblies for enhancing efficiency and stability of wastewater treatment systems.

In general, the present disclosure provides for a novel global sensing technology utilizing a microelectrode array ("MEA") to solve various problems of monitoring wastewater treatment systems.

The present disclosure provides for improved systems/methods for monitoring wastewater treatment systems, with the improved systems/methods obtaining a substantially complete global profile of multiple parameters simultaneously. More particularly, the present disclosure provides that by patterning multiple electrodes (e.g., mm-sized electrodes) on a film (e.g., thin plastic film), a MEA can monitor multiple parameters simultaneously in 2-dimension (2-D) of a given system so that global dynamic stratification inside such systems can be real-time visualized for swift response under various wastewater conditions.

The present disclosure provides for an array of printed microelectrodes to test wastewater. Printed electrodes have not been used in environmental engineering, much less an array of electrodes. Waste tanks, anaerobic or aerobic, are delicately balanced and can take months to be completely processed. If bacteria die or get sour, it can be time-consuming and costly to fix. Typical single electrodes can only test at one localized spot, which may not catch a problem until too late. An exemplary array of microelectrodes can catch the full depth and with better understanding what is happening in the tank, and the printed technology on film (e.g., plastic) is much more durable and cheaper. An array is also able to test multiple parameters (e.g., pH, temperature, oxygen, conductivity, etc.).

In addition, an EPA regulation will require most wastewater systems to be retrofitted, and the EPA would like to have 11,000 from the now 2000 anaerobic digestor tanks for other wastes (e.g., food systems from restaurant, dairy farms, supermarkets, etc.) In general, the U.S. is behind on waste cleanup (Germany has 8000 AD tanks). A viable market for exemplary embodiments/assemblies of the present disclosure is the anaerobic tanks, but can be broadened to aerobic tanks, sludge tanks, chlorination tanks, etc.

The end-products of the process can also be sold (e.g., as fuel, heating systems, etc.), so it is in the best interest of the companies to be diligent about the monitoring.

Current electrodes can only test one variable, so such users need multiple electrodes. In addition, conventional electrodes are fragile (e.g., made of glass micro-pipettes) and break easily, especially in thicker sludge. They are also expensive and take a long time to make (e.g., \$25,000 for four probes.) The exemplary assemblies of the present disclosure are cheaper, more durable, more efficient, and give better/improved data.

The present disclosure can utilizes anaerobic digestion ("AD") as a first test site for exemplary MEAs. But, the MEAs are not only for AD systems, they can be applied to a broad ranges of diverse water/wastewater treatment systems or the like.

For exemplary MEA mechanisms, each mm-sized electrode works independently, with its own working and reference electrodes, all tightly and precisely printed together on the film. For the oxygen electrode, it measures current. For the pH electrode, it measures potential. For the conductivity electrode, it measures the capacitors. For the temperature electrode, it measures resistance.

Wastewater has historically been treated as waste when in fact it is rich in water, nutrients, and energy. The future of waste industry lies in its ability to derive value from natural resources embedded in wastewater. AD technology offers a waste management and energy solution to municipalities across the U.S. by converting waste streams into valuable energy which creates financial value. There are about 2000 AD systems in the U.S., with a goal of building 11,000 AD systems in the next two decades. In the meantime, stringent environmental regulations require high performance of waste treatment systems, and exert enormous demands for real-time monitoring devices. The waste industry yields a huge market value over 1 trillion dollars. There are over 14,000 municipal wastewater treatment plants ("WWTPs") nationwide, around 70% of which need to be retrofitted in the next decade with an estimated infrastructure investment of \$110 billion. These retrofit and new systems offer a vast market potential for cutting-edge monitoring technology, and MEA has the edge as the front runner in this new wave.

MEAs have a broad customer pool in the waste treatment market. The present disclosure can use anaerobic digestion (AD) as a first test site for MEA technology, since the heterogeneous gas/liquid/solid phases provide a nice scenario to use global profiles. AD technology has drawn a global interest for the treatment of waste streams originating from service industries (e.g. restaurant, supermarkets), dairy farms (e.g., milk, ice-cream manufacturing), and municipalities. Due to the extensive usages of biogas/liquid/biosolid products from AD systems, their efficient and stable operation yields tremendous economic, environmental, and energy significance.

The present disclosure provides for a sensor assembly including a substrate, the substrate having a length and a width; a plurality of micro-electrodes deposited on the substrate, the substrate configured to be at least partially disposed within and along the depth of a water treatment system; wherein the plurality of micro-electrodes is configured and adapted to facilitate the simultaneous detection of multiple parameters along the depth of the water treatment system.

The present disclosure also provides for a sensor assembly wherein the substrate is a flexible plastic film. The present disclosure also provides for a sensor assembly wherein each micro-electrode of the plurality of micro-electrodes is a mm-sized electrode. The present disclosure also provides for a sensor assembly wherein each micro-electrode of the plurality of micro-electrodes includes gold or silver.

The present disclosure also provides for a sensor assembly wherein the water treatment system is selected from the group consisting of aeration tanks, anaerobic digestors, anoxic tanks, storage tanks, pipelines, sedimentation tanks, sludge tanks, chlorination tanks, watershed sites and sediment restoration sites.

The present disclosure also provides for a sensor assembly wherein the plurality of micro-electrodes includes from about 48 to about 500 micro-electrodes deposited on the substrate.

The present disclosure also provides for a sensor assembly wherein the multiple parameters are selected from the group consisting of oxygen parameters, pH parameters, temperature parameters, conductivity parameters, redox potential parameters, ammonium parameters, metal ion parameters, pesticide parameters, salt parameters and nutrient parameters. By way of example, pesticide parameters include organophosphates and their degradation products, e.g., methyl-azinphos; demeton; diazinon; disulfoton, ethion, malathion, parathion, ethyl-parathion, methyl-parathion, and paraoxon Examples of nutrient parameters include ammonium ($NH_4^+$), nitrate ($NO_3^-$), nitrite ($NO_2^-$) and phosphate ($PO_4^{3-}$).

The present disclosure also provides for a sensor assembly wherein each micro-electrode of the plurality of micro-electrodes has a length of about 5 mm and a width of about 5 mm on the substrate. The present disclosure also provides for a sensor assembly wherein the plurality of micro-electrodes includes printed micro-electrodes.

The present disclosure also provides for a sensor assembly wherein the substrate includes multiple different parameter detecting micro-electrodes aligned in multiple horizontal and vertical rows along the length and width of the substrate.

The present disclosure also provides for a method for utilizing a sensor assembly including providing a substrate, the substrate having a length and a width; depositing a plurality of micro-electrodes on the substrate; disposing the substrate at least partially within and along the depth of a water treatment system; and operating the plurality of micro-electrodes to simultaneously detect multiple parameters along the depth of the water treatment system.

The present disclosure also provides for a method for utilizing a sensor assembly wherein the substrate is a flexible plastic film. The present disclosure also provides for a method for utilizing a sensor assembly wherein each micro-electrode of the plurality of micro-electrodes is a mm-sized electrode. The present disclosure also provides for a method for utilizing a sensor assembly wherein each micro-electrode of the plurality of micro-electrodes includes gold or silver.

The present disclosure also provides for a method for utilizing a sensor assembly wherein the water treatment system is selected from the group consisting of aeration tanks, anaerobic digestors, anoxic tanks, storage tanks, pipelines, sedimentation tanks, sludge tanks, chlorination tanks, watershed sites and sediment restoration sites.

The present disclosure also provides for a method for utilizing a sensor assembly wherein the plurality of micro-electrodes includes from about 48 to about 500 micro-electrodes deposited on the substrate.

The present disclosure also provides for a method for utilizing a sensor assembly wherein the multiple parameters are selected from the group consisting of oxygen parameters, pH parameters, temperature parameters, conductivity parameters, redox potential parameters, ammonium parameters, metal ion parameters, pesticide parameters, salt parameters and nutrient parameters.

The present disclosure also provides for a method for utilizing a sensor assembly wherein each micro-electrode of the plurality of micro-electrodes has a length of about 5 mm and a width of about 5 mm on the substrate. The present disclosure also provides for a method for utilizing a sensor assembly wherein depositing the plurality of micro-electrodes on the substrate includes printing the plurality of micro-electrodes on the substrate.

The present disclosure also provides for a method for utilizing a sensor assembly wherein the substrate includes multiple different parameter detecting micro-electrodes aligned in multiple horizontal and vertical rows along the length and width of the substrate.

Any combination or permutation of embodiments is envisioned. Additional advantageous features, functions and applications of the disclosed assemblies, systems and methods of the present disclosure will be apparent from the description which follows, particularly when read in conjunction with the appended figures. The references, publications and patents listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure. To assist those of ordinary skill in the art in making and using the disclosed assemblies, systems and methods, reference is made to the appended figures, wherein:

FIG. 2A shows the whole ME system setup; and FIG. 2B shows penetration of a ME into an activated sludge floc;

FIG. 11A shows an MEA response to the changes of conductivity and temperature in water solution;

DETAILED DESCRIPTION OF THE DISCLOSURE

Figure 1A:
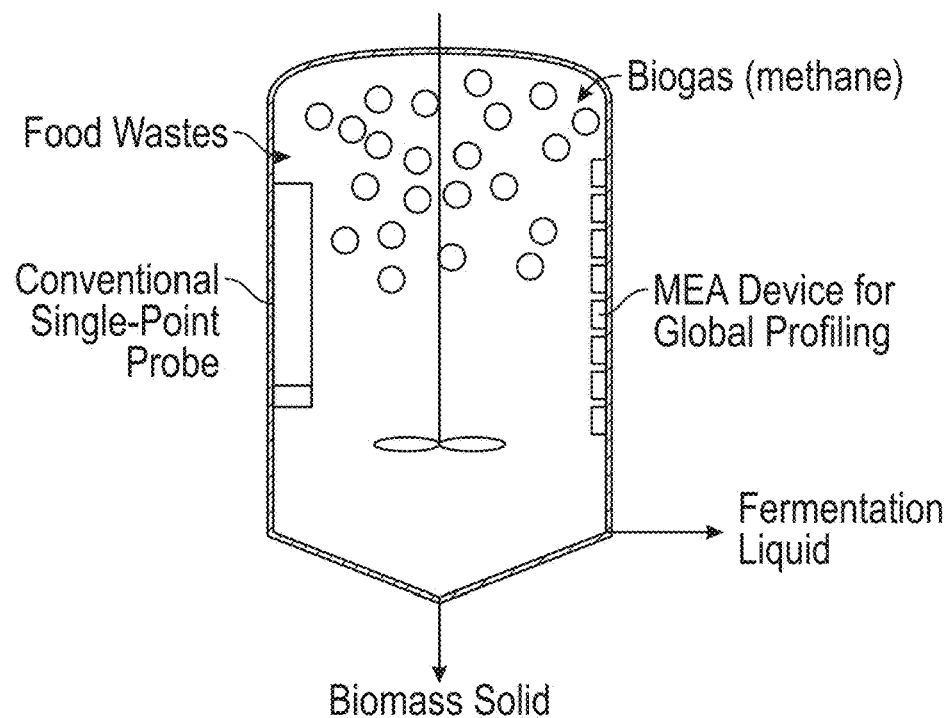
FIGS. 1A and 1B show a comparison of a conventional single point probe and an exemplary global profiling MEA in an anaerobic digestion (AD) system in FIG. 1A, and the illumination along the system depth in FIG. 1B.

Exemplary embodiments disclosed herein are illustrative of advantageous sensor assemblies, and systems of the present disclosure and methods/techniques thereof. It should be understood, however, that the disclosed embodiments are merely exemplary of the present disclosure, which may be embodied in various forms. Therefore, details disclosed herein with reference to exemplary systems/assemblies and associated processes/techniques of assembly and use are not to be interpreted as limiting, but merely as the basis for teaching one skilled in the art how to make and use the advantageous assemblies, systems and methods of the present disclosure.

The present disclosure provides advantageous sensor assemblies. More particularly, the present disclosure provides microelectrode array ("MEA") real-time in situ global sensing assemblies for enhancing efficiency and stability of wastewater treatment systems. The present disclosure further provides for a novel global sensing technology utilizing a microelectrode array (MEA) to solve various problems of monitoring wastewater treatment systems.

As noted above, current practice provides that some wastewater treatment systems use conventional single-point sensing technologies, which generally can only measure one parameter at a sampling site. As such, this type of sensing generally can only obtain local information at a single point of wastewater treatment systems, which inhibits swift and efficient action under various upcoming events and can lead to low efficiency and malfunction of systems.

In exemplary embodiments, the present disclosure provides for improved systems/methods for monitoring wastewater treatment systems, with the improved systems/methods obtaining a substantially complete global profile of multiple parameters simultaneously. More particularly, the present disclosure provides that by patterning multiple electrodes (e.g., mm-sized electrodes) on a film (e.g., thin plastic film), a MEA can monitor multiple parameters simultaneously in 2-dimension (2-D) of a given system so that global dynamic stratification inside such systems can be real-time visualized for swift response under various wastewater conditions, thereby providing significant operating and commercial advantages as a result.

The end users of the disclosed MEA technology are quite broad, ranging from diverse operational systems (e.g., aeration tanks, sedimentation tanks, sludge tanks, chlorination tanks) in municipal wastewater treatment plants, food waste anaerobic digestors ("AD"), water/wastewater pipeline networks to watershed and sediment restoration sites. Currently, these waste/wastewater treatment facilities generally use single point probe technology, and many parameters have to be measured off line and ex situ, leading to severe lag-time action after shocks. Once wastewater treatment systems suffer from malfunction, it can take at least a couple of days or even months to recover back to normal operational status, which causes severe environmental pollution and public health concerns.

The MEAs of the present disclosure can provide real-time in situ global profiles of multiple critical parameters for water/wastewater treatment systems. Existing sensing technologies cannot achieve such function. In addition, the U.S. EPA has a stringent regulation (e.g., total nitrogen ("TN") less than 10 mg/L and total phosphorous ("TP") less than 0.5 mg/L) for effluent discharge, meaning that more than 70% of existing wastewater treatment systems need to retrofit in next two decades. In the meantime, there are about 2000 AD systems in the U.S., with a goal of building 11,000 AD systems in next two decades. These retrofit and new systems offer a vast market potential for cutting-edge monitoring technology, and the exemplary MEA technology fits well into this opportunity.

MEAs have a broad customer pool in the waste treatment market. The present disclosure can start with anaerobic digester (AD) as the testbed for MEA, since the heterogeneous gas/liquid/solid phases in AD systems provide a nice scenario to use global profiles. AD technology has drawn a global interest for the treatment of waste streams originating from service industries, dairy farms, and municipalities. However, the performance of AD systems is far below designed expectations. The connection between biogas/liquid/solid phases can be unclear, mainly due to infrequent localized information obtained from single point probes. By installing MEAs along the AD depth, 2-D profiles of multiple critical parameters (e.g., pH, temperature, conductivity, oxygen) can be obtained simultaneously, leading to real-time capture of system operational status and early warnings before malfunction.

Figure 2A:
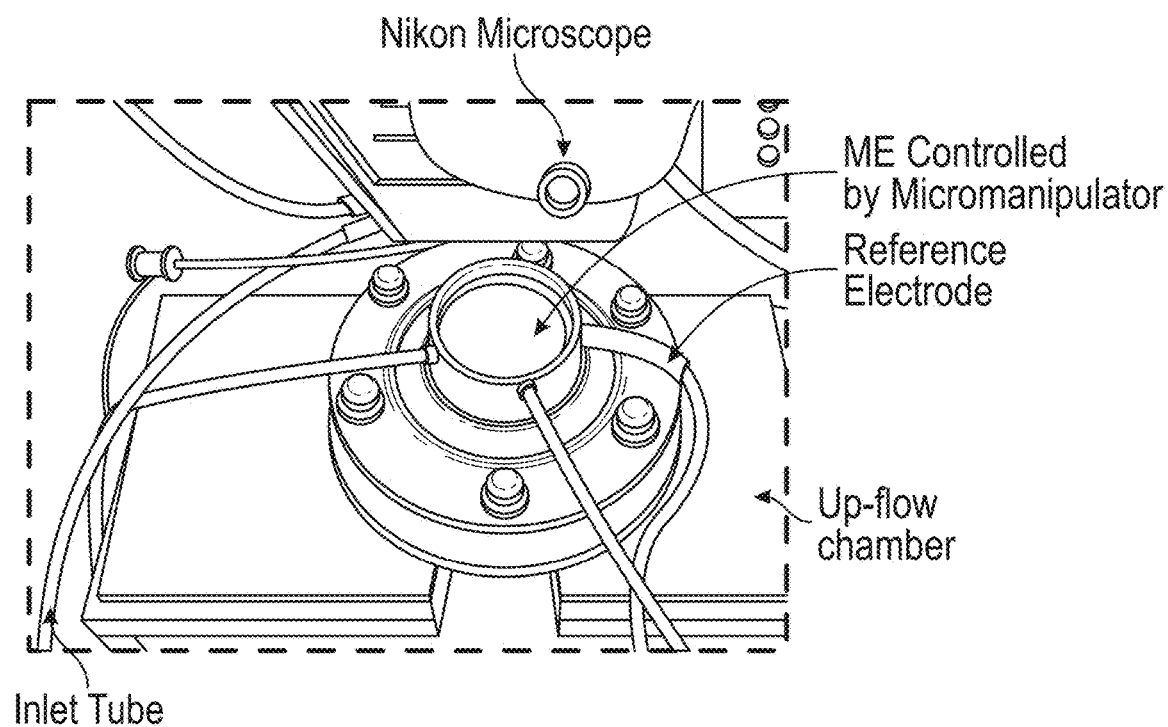
FIGS. 2A and 2B show the experimental setup of a needle-shape microelectrode (ME) measurement of activated sludge floes.
Figure 2B:
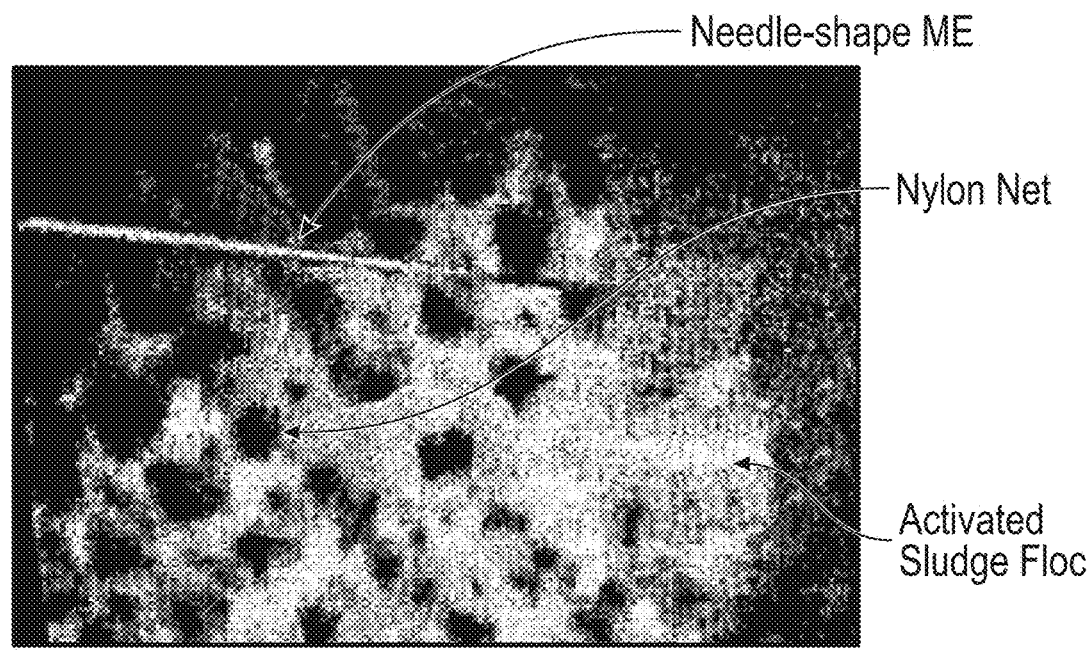

Micro-electrodes ("MEs") have been developed in the past two decades to probe inside the micro-environment of biological samples (e.g., activated sludge flocs, and biofilms). Many existing MEs are micro-pipette needle-shaped (FIG. 2). The needle-shaped MEs have at least three major problems hindering the real-time measurement in waste treatment systems. First, the number of species detected can depend on the ME characteristics and may be limited. MEs may only measure a single parameter and only obtain one data point during each penetration into a sample, which makes it substantially not possible for real-time measuring/profiling the effects of shocks. Second, these MEs can require tedious fabrication procedures.

In general, fabrication has a low success rate and reproducibility. MEs are fragile and may not be reusable for multiple measurements. So far, MEs are mainly used in bench-scale lab measurements without any real-world application in waste systems. Third, the whole ME setup can be complicated. The movement of MEs can be controlled by a bulky micro-manipulator (more than 100 lbs and 3 feet high) (FIG. 2), making it substantially not possible for the in situ measurement at wastewater treatment plants or watershed sites.

Figure 1B:
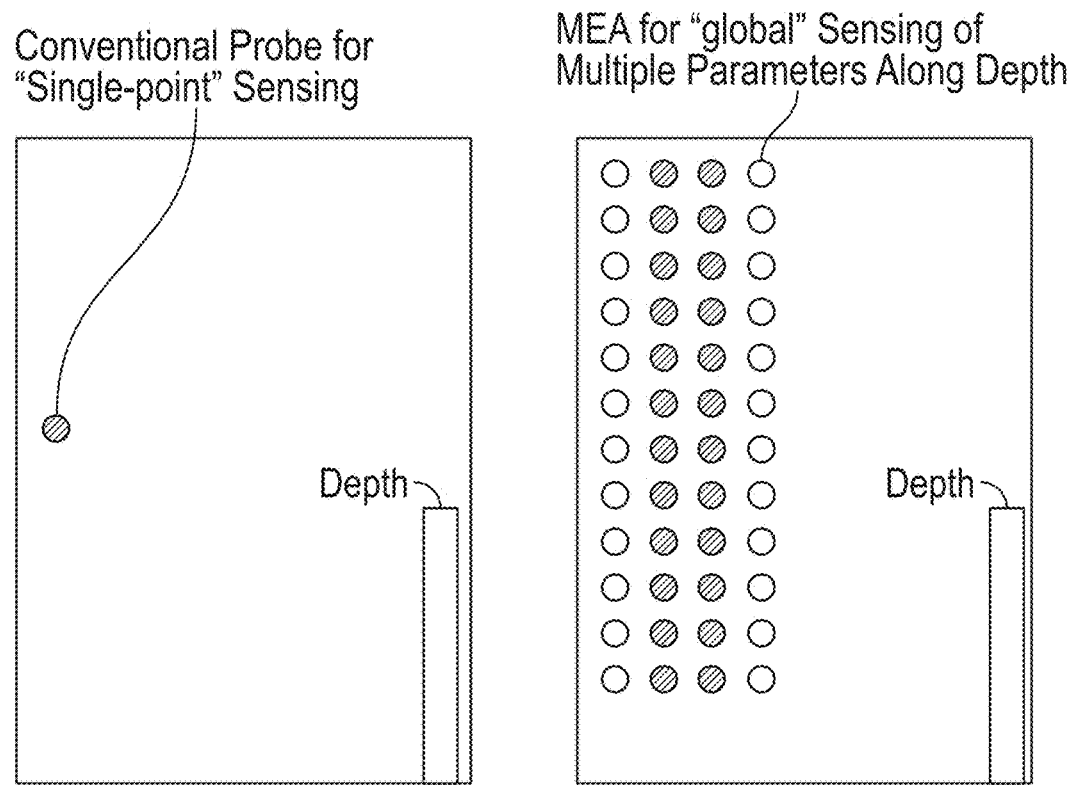

Using an anaerobic digestion ("AD") system as an example, conventional single point can only measure a single type parameter (e.g., oxygen or pH or temperature) at a single point inside the AD system (FIGS. 1A-1B), through which only local information can be obtained. In contrast, a MEA assembly can easily host 300 to 500 mm-sized electrodes on a piece of plastic film (e.g., size of an A4 paper), and obtain a 2-D global profile of multiple parameters (e.g., oxygen, pH, and temperature) along the depth of the AD system/tank (FIG. 1B). As such, the heterogeneous phases in AD systems, including biogas/liquid/biomass solid can be real-time in situ visualized. This exemplary global sensing technology of water systems can provide a substantially complete data set of AD system operational status, first-hand information for global changes of the AD system, early degradation warning, and thus enhancing AD system stability under transient shocks (FIG. 1B). By patterning multiple pieces of mm sized multi-type electrodes (e.g., 0.50 cm×0.50 cm) on a plastic film, the MEAs exponentially reduce the space with an A4 paper size film (e.g., film size can be 30 cm×20 cm) hosting at least 300 electrodes, and thus greatly easing the deployment and reducing the cost (around $1.0 for a mm-sized electrode). In addition, the micro-watt ($\mu$W) requirement of MEAs substantially reduces power input. All of these advantages offer MEA assemblies a substantially unbeatable global monitoring/profiling technology of water systems or the like.

Wastewater treatment efficiency and stability heavily rely on swift action taken under dynamic conditions (e.g., influent wastewater types, quality/quantity changes, temperature drop, pH drop, toxic metal spikes). Currently, these actions are lag-time performed based on wastewater quality parameters monitored by electrodes installed in the systems. Conventional single point probes can only get localized information, without the complete picture of operational status. To solve this critical monitoring problem, the present disclosure provides for MEA assemblies having patterned multiple mm-sized electrodes by precise printing designs and that achieve global sensing of multiple parameters simultaneously in 2-D of water systems (FIGS. 1 and 3). As such, a substantially complete picture of systems can be obtained and swift action can be taken under dynamic conditions.

The exemplary MEA assemblies have several distinct advantages over traditional single-point probes and MEs. First, they provide for a simple fabrication procedure. The present disclosure provides for inkjet-printing technology to print the precisely-designed mm-sized electrodes on a plastic film. In exemplary embodiments, the whole printing process only takes less than 2 hours for one sheet of plastic film hosting 100 to 200 electrodes, which makes the mass fabrication of MEAs possible. Traditional MEs take at least 5 to 6 hours (even overnight) to fabricate a single ME.

Second, the exemplary MEA assemblies provide a sturdy configuration for reuse. MEA assemblies fabricated by inkjet-printing are mechanically strong and durable for long-term monitoring. Lab-scale tests have shown stable performance over a 2-month operational period. In contrast, MEs made by glass pipette can only last for a couple days and are easily broken when touching a hard surface.

Third, the exemplary MEA assemblies provide for compact measurement devices/assemblies for field work. By precisely patterning and aligning on the film (FIG. 3), the position of each electrode on the MEA is known without the need of a bulky micro-manipulator.

Moreover, the exemplary MEA assemblies provide for the in situ global profiling of multiple parameters of the systems. This is an unique advantage of the exemplary MEA assemblies compared with the existing electrodes/multi-meters/MEs that can only measure parameters at a single point. The present disclosure provides that with multiple types of electrodes (e.g., oxygen, pH, temperature and conductivity) aligned at multiple rows on the assemblies, global profiling of systems is possible. In addition, a MEA on a plastic film is very easy to mount inside waste treatment systems.

Furthermore, the exemplary MEA assemblies provide for low power consumption. Unlike existing multi-meters (consisting of multiple macro-sized electrodes) that can require 1 to 10 W, exemplary MEAs can only require micro-watt power requirements.

The exemplary MEA assemblies possess several commercial attractions that existing probes do not offer. For example, the exemplary MEA assemblies provide a simple compact structure with a thin plastic film hosting hundreds of mm-sized multiple-type electrodes in multiple rows.

Moreover, the exemplary MEA assemblies provide the capability of global profiling multiple parameters in a given system. The real-time in situ profiles promptly indicate the system operational status, which facilitate swift and efficient action under dynamic incoming waste events and unexpected shocks, and ultimately maintain the system global stability.

Furthermore, the exemplary MEA assemblies provide long-term durability. Exemplary inkjet-printed MEAs and plastic films are mechanically strong and durable even under harsh conditions (e.g., soil, waste solution). The exemplary MEA assemblies have good sensitivity that has been well proven in lab-scale tests.

Figure 3A:
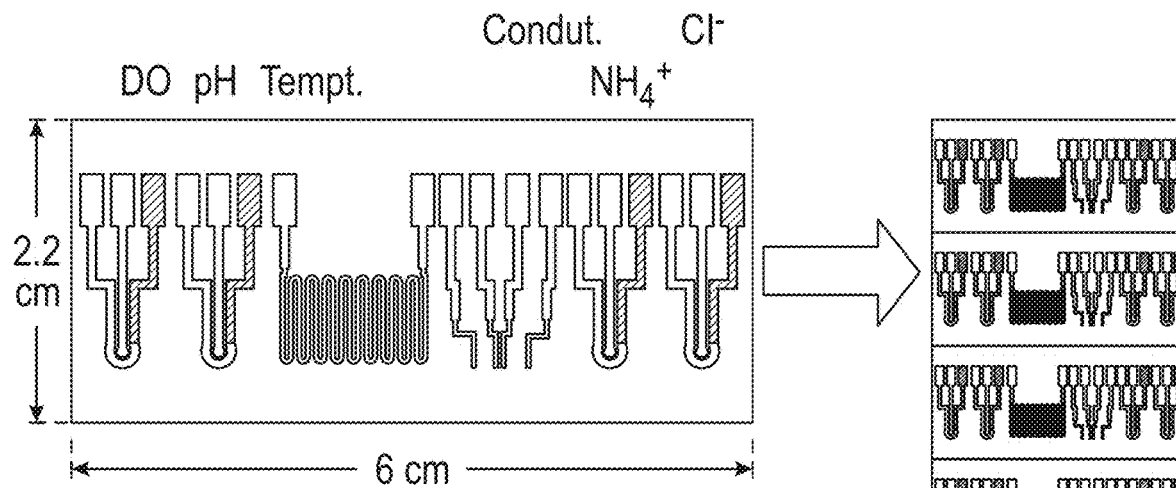
FIGS. 3A-3B show a MEA inkjet-printed on a film for real time in situ profiling of multiple parameters.
Figure 3B:
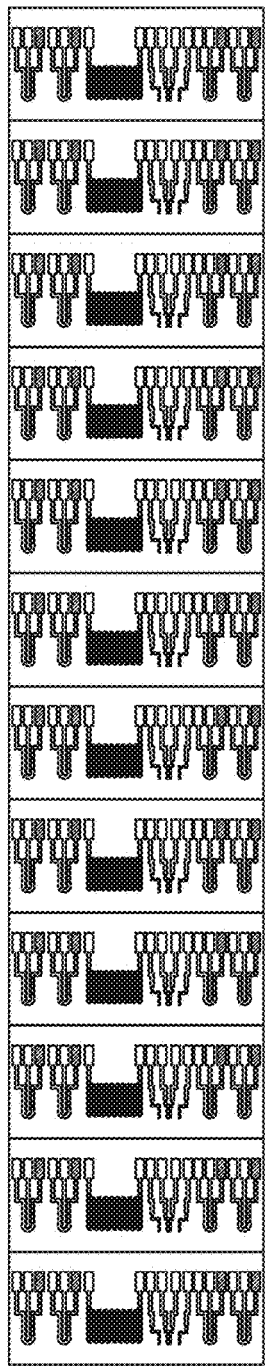

Exemplary MEA assemblies have been successfully fabricated. Specifically, the gold and carbon ink prepared for each type of mm-sized electrode (e.g., oxygen, pH) can be inkjet printed on a plastic film with precise design (FIGS. 3A and 3B). Different types of electrodes are laid out in a row. Multiple rows vertically compose a MEA matrix capable of simultaneously measuring multiple parameters along the depth (e.g., 4 cm (width)×30 cm (depth) hosting 40 electrodes) of the system/tank. Compared with conventional probes/electrodes measuring single data at a single sampling point, the exemplary MEA possesses distinct advantages of multiple-parameter monitoring, global profiling, high accuracy, easy fabrication, and high sensitivity.

Figure 4:
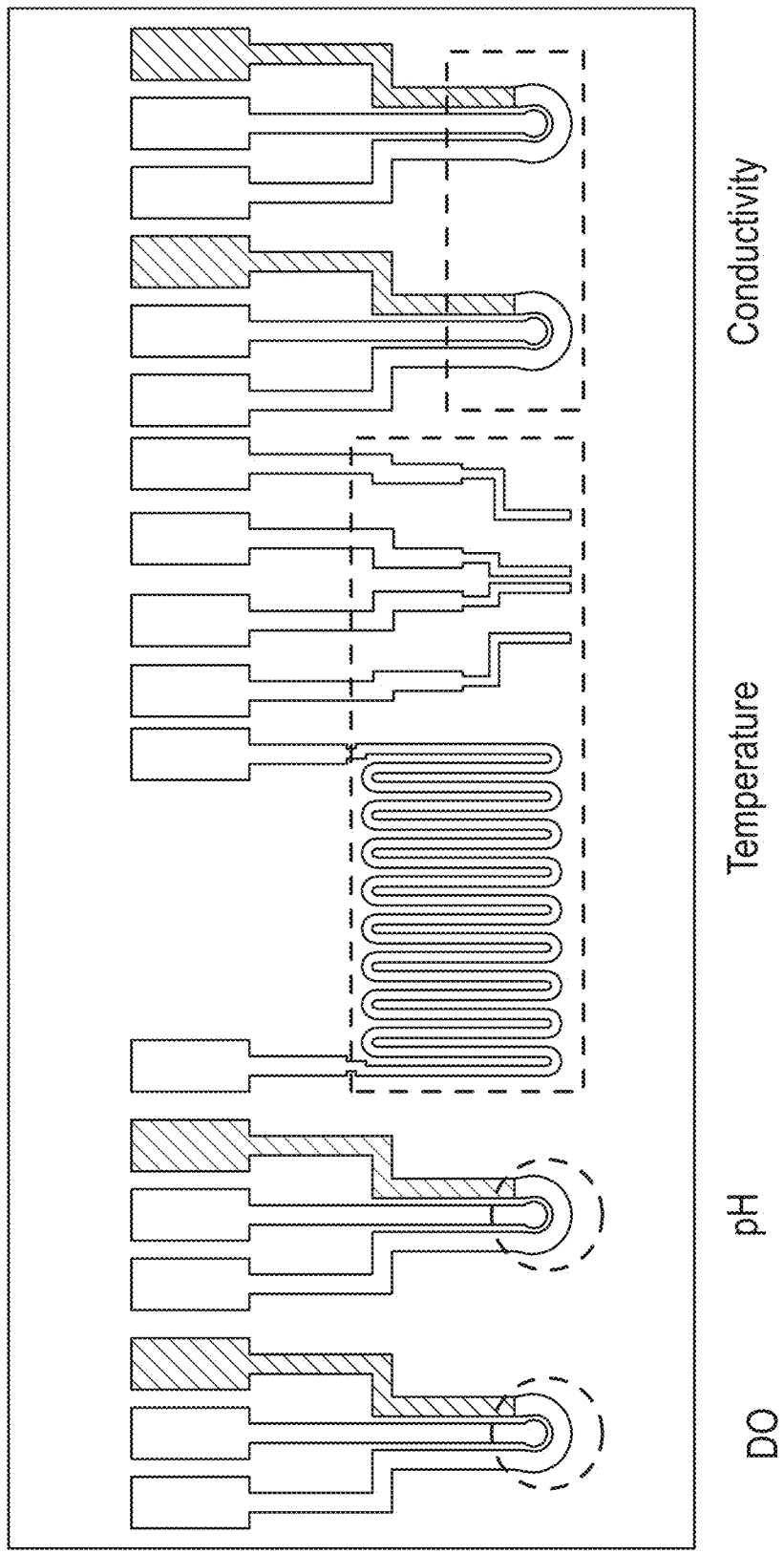
FIG. 4 shows details of each exemplary type mm-sized electrodes (dissolved oxygen ("DO"), pH, temperature and conductivity) printed on a plastic film.

A core technology of an exemplary MEA is the precisely-designed inkjet printed mm-sized electrode (as shown in FIGS. 3A and 3B). Details for each exemplary type of mm-sized electrode are presented in FIG. 4. Inkjet-printing has been developed for making chemical catalysts and electrochemical materials, and has not been applied for fabricating mm-sized electrodes. In fact, printing mm-sized electrode is not just shrinking macro-sized electrodes into small sizes. Sensor materials had to be developed to be smoothly printed through ink-jet printers. An exemplary MEA developed provided by the present disclosure can be mainly fabricated by gold/silver ink and carbon ink. Aligning multiple mm-sized electrodes can be designed using a CAD program.

Figure 5A:
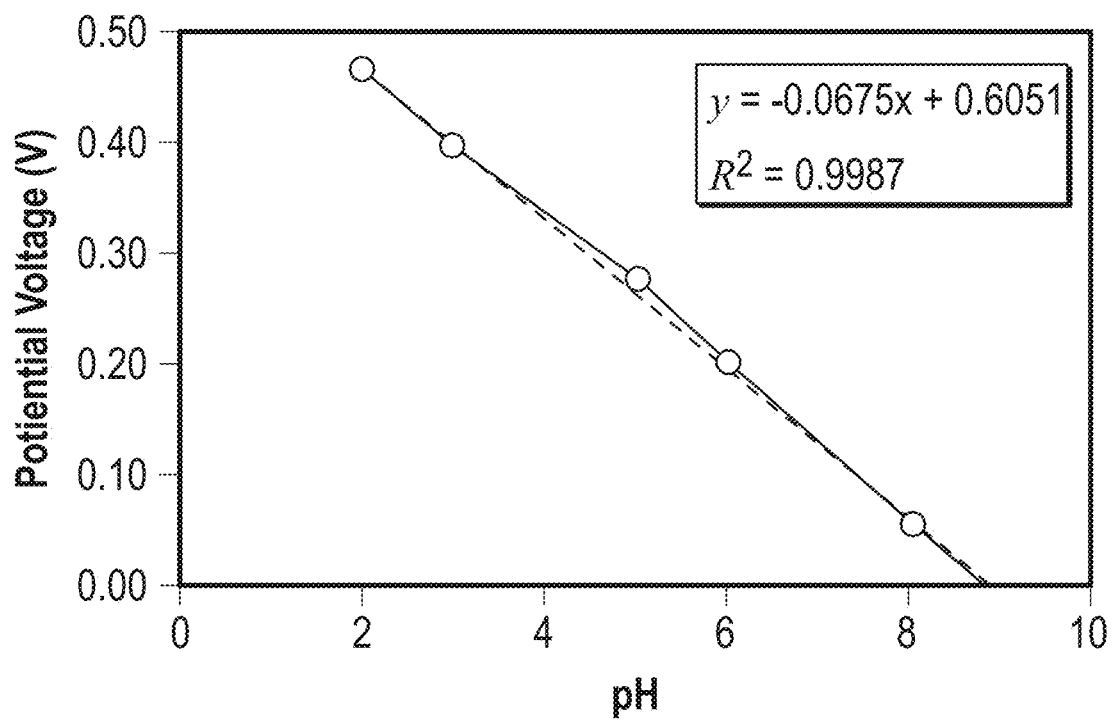
FIG. 5 shows a MEA calibration curve of pH.
Figure 5B:
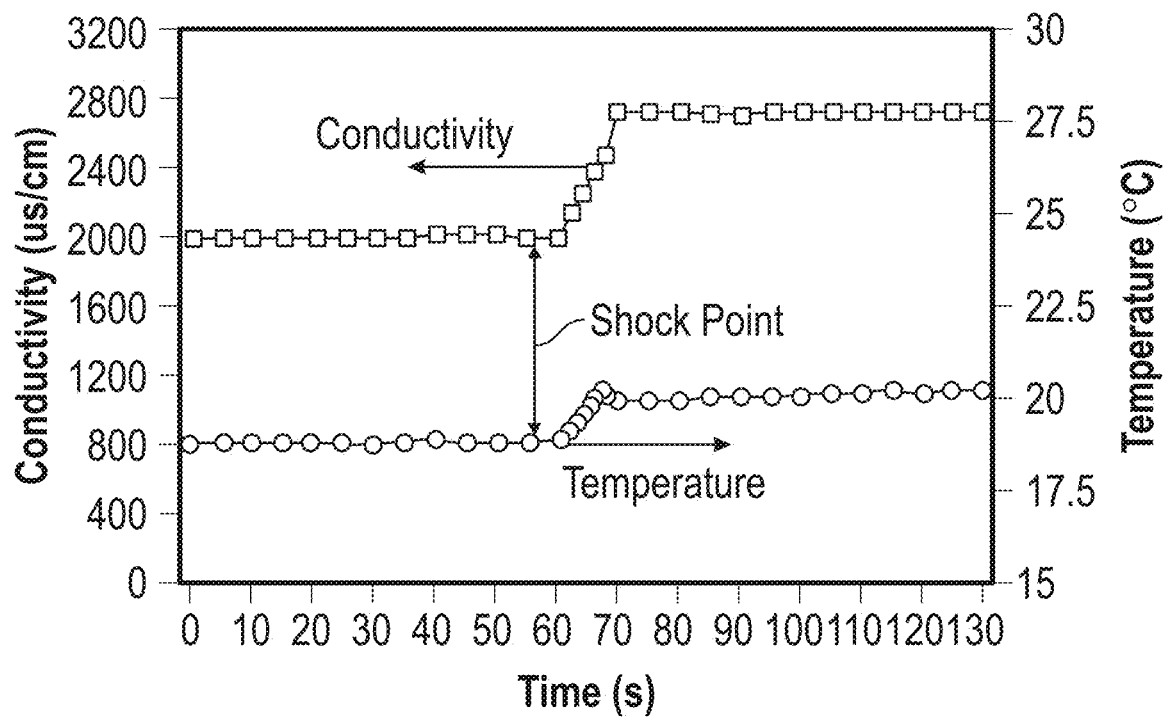
Figure 6A:
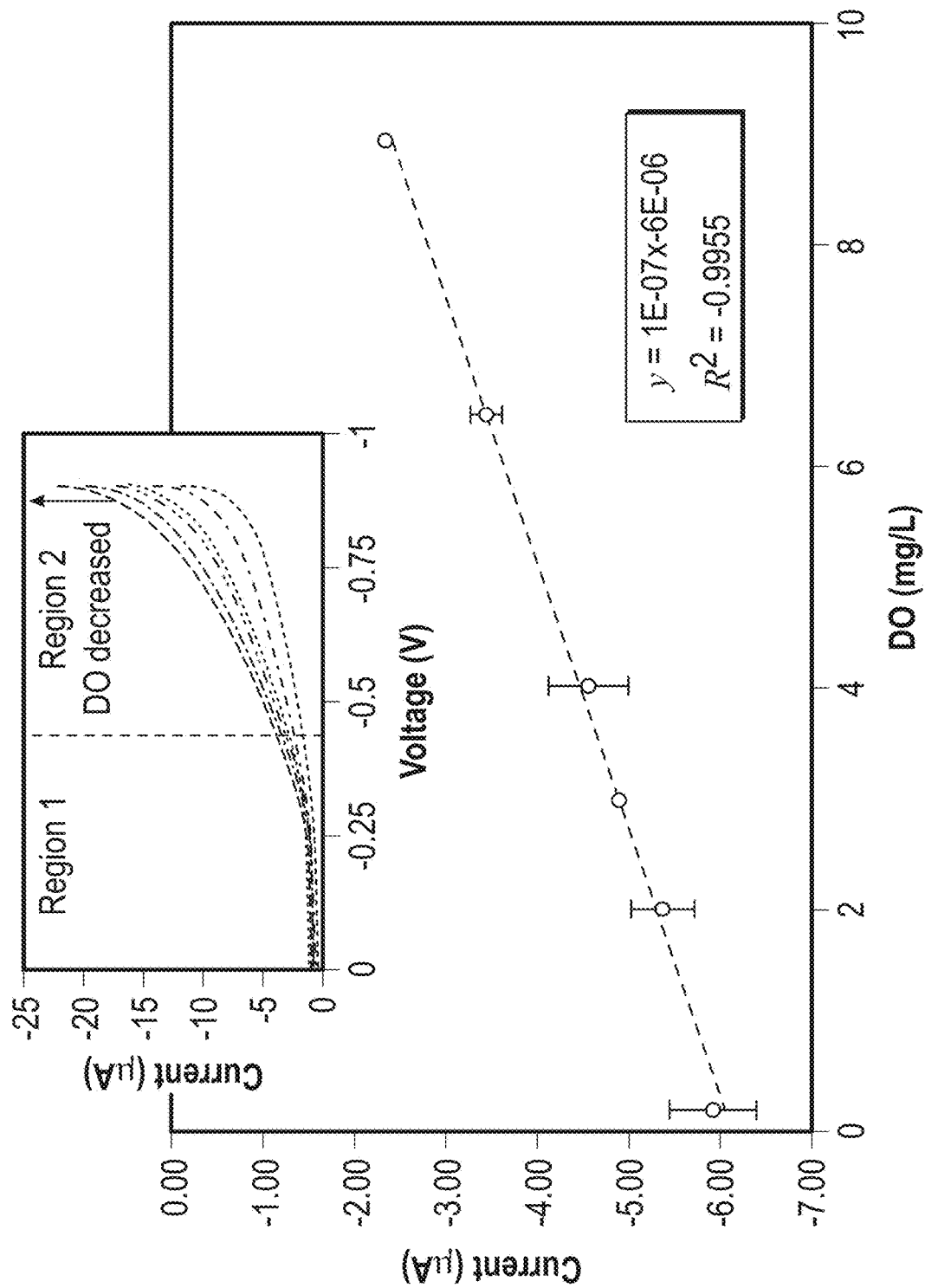
FIG. 6A shows calibration curve of dissolved oxygen (DO) MEA sensor, including plots for Region 1 and Region 2.
Figure 6B:
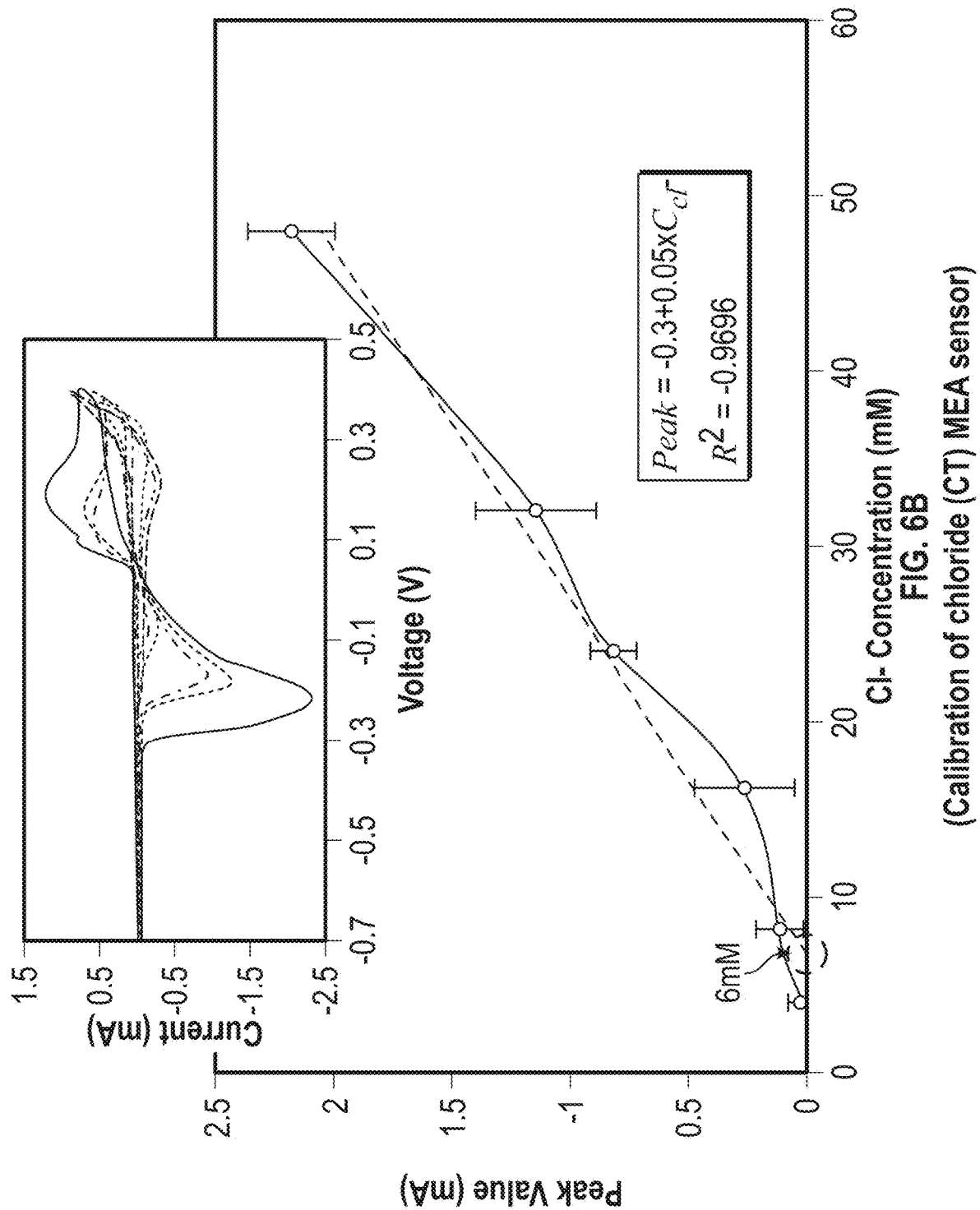
FIG. 6B shows calibration curve of chloride (CY) MEA sensor.
Figure 7:
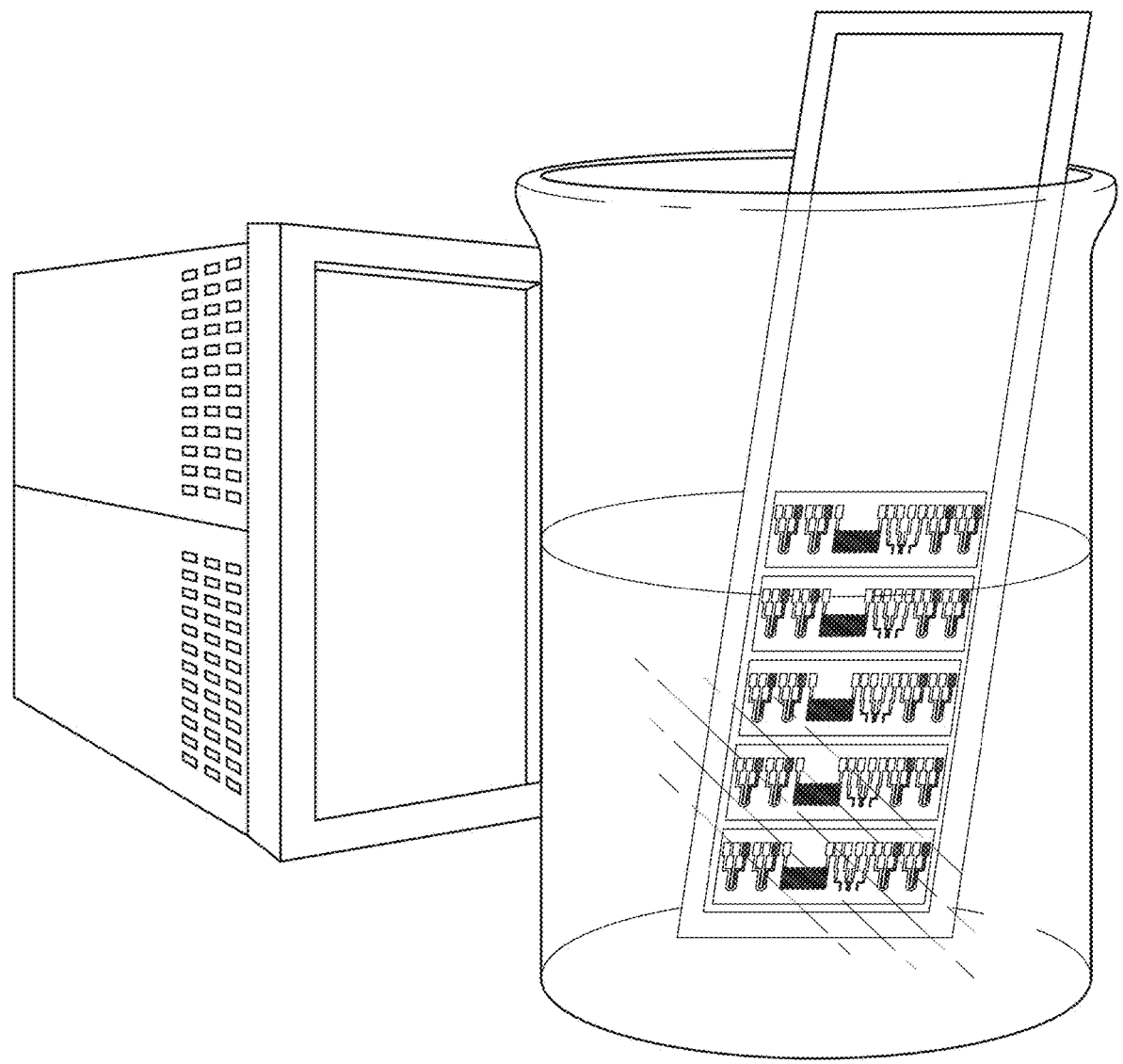
FIG. 7 shows the insertion of a MEA plate into a system as an exemplary setup demonstration.

Some important parameters for MEAs include sensitivity, reusability, signal recovery, and mechanic stability. Tests have thoroughly calibrated the MEAs in water solution and showed high $R^2$ values (FIG. 5). FIGS. 6A and 6B provide exemplary calibration curves for MEA sensors. Specifically, FIG. 6A provides a calibration curve of dissolved oxygen (DO) MEA sensor, including plots for Region 1 and Region 2, and FIG. 6B provides a calibration curve of chloride (CY) MEA sensor. FIG. 7 shows an exemplary setup demonstration of deploying a MEA plate into a system (e.g., using a beaker to clearly show the inside details).

The present disclosure advantageously provides for an electrode array equipped with multiple mm-sized electrodes at multiple rows that can measure multiple parameters in 2-dimension (2-D) simultaneously.

The exemplary MEA assemblies have great potential for renovating wastewater treatment system real-time sensing and improving system stability and efficiency. The present disclosure also provides for market expansion in the waste treatment industry.

The present disclosure will be further described with respect to the following examples; however, the scope of the disclosure is not limited thereby. The following examples illustrate, inter alia, exemplary advantageous sensor assemblies, and related methods of use.

Example 1

The present disclosure provides for the development of a durable, inexpensive milli-electrode array (MEA) technology/assembly by employing multiple mm-sized electrodes on a flexible plastic film that can be easily installed inside waste treatment systems to rapidly profile multiple parameters with high temporal and spatial resolution.

Figure 8:
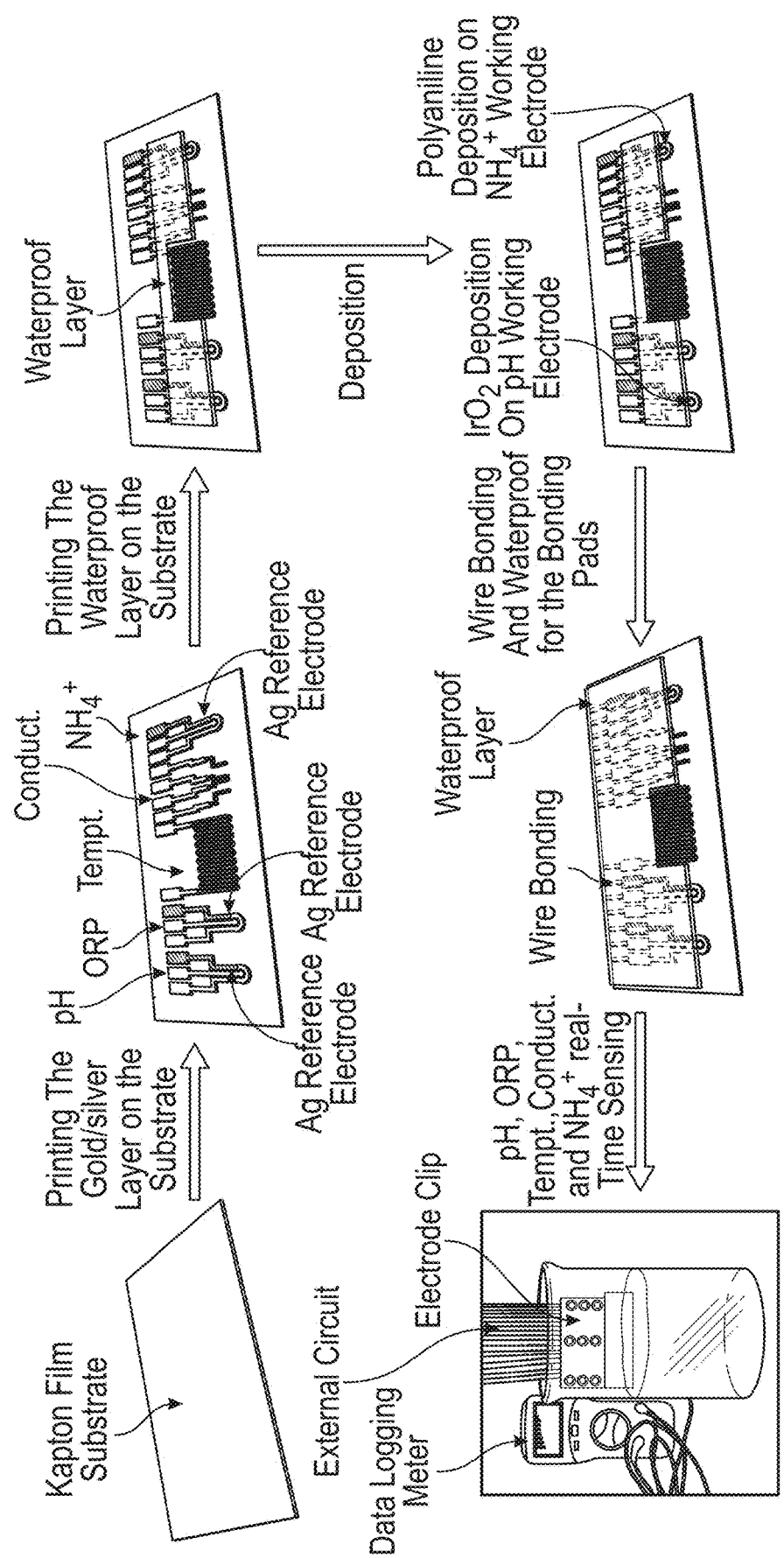
FIG. 8 shows an exemplary milli-electrode array (MEA) that includes five types of mm-sized electrodes.

For exemplary MEA assembly fabrication, gold and carbon ink prepared for each type of mm-sized electrode can be precisely printed on a flexible Kapton film using an ink-jet printer (FIG. 8). Different types of electrodes are laid out in a row. Multiple rows of mm-sized electrodes vertically compose a MEA matrix capable of simultaneously measuring multiple parameters along system depth, and thus elucidating the heterogeneous status inside systems.

The horizontal distance between each type of electrodes can be 0.30 cm, which is far enough apart to prevent the interference between different types of electrodes during measurement. Each electrode has a bond pad on the top of the chip for wire bonding, allowing the easy connection to an external circuit. An epoxy glob top is applied to protect the bond wires from mechanical damage and wet working environments. The surface of the MEA sensors can be fully coated with a waterproof layer (e.g., poly(amic acid) ink) to protect the electrodes in wastewater. For installation into waste treatment systems (e.g., aeration tanks, anaerobic digestors, etc.), the flexible film with the printed MEAs can be bonded on a round stick and easily inserted into the system through an installation port.

Figure 9:
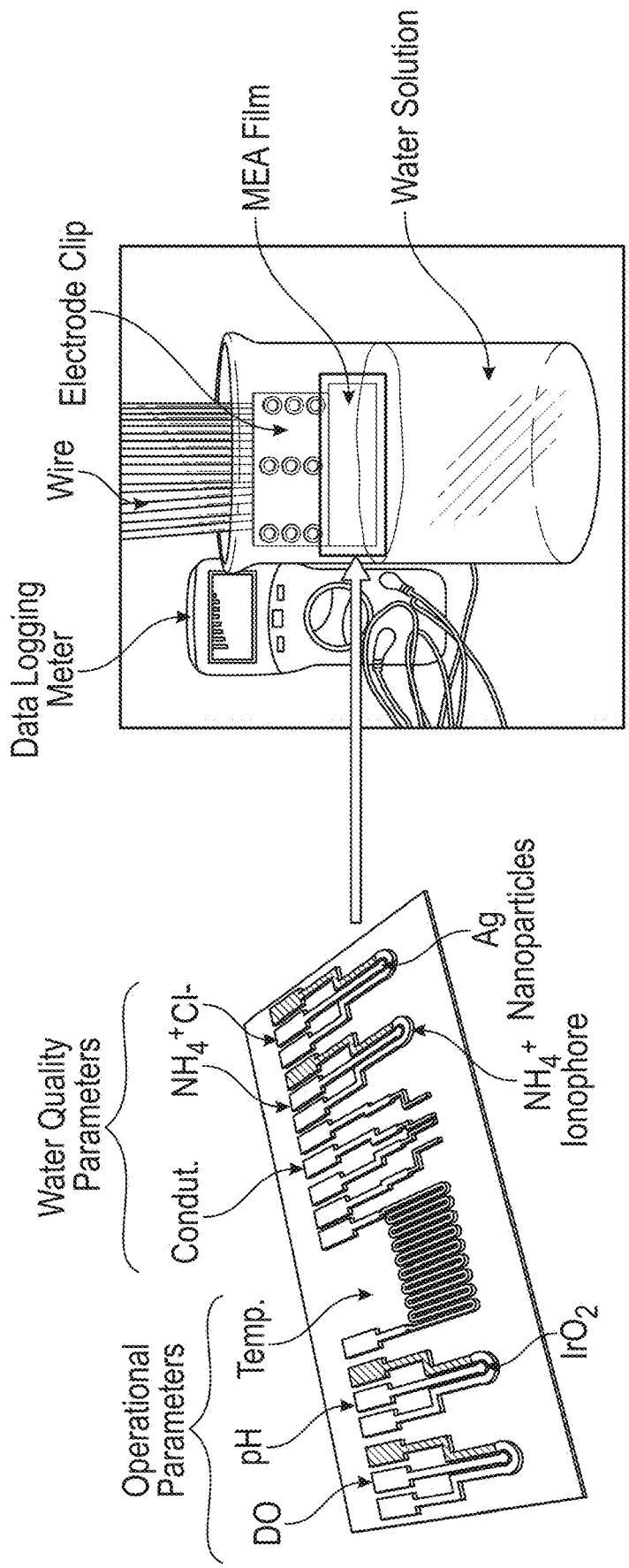
FIG. 9A shows a schematic of exemplary 6-type MEA sensors that are ink-jet-printed/integrated on a film for real time in situ profiling of multiple parameters.
FIG. 9B shows an exemplary lab-test demonstration of the exemplary MEA sensors of FIG. 9A.

Five types of exemplary MEA sensors (e.g., redox potential (ORP), pH, temperature, conductivity, and ammonium $NH_4^+$) specifically for wastewater anaerobic treatment have been developed by precisely patterning multiple mm-sized electrodes using an inkjet printer (FIG. 9A).

Multiple rows vertically compose a MEA matrix capable of simultaneously measuring multiple parameters along system depth (e.g., 4 cm (width)×30 cm (depth) hosting 60 electrodes) (FIG. 9B). Each type electrode can be modified for a specific parameter using the reported procedures, with a bond pad on the top of the film for wire bonding, allowing for an easy connection to an external circuit (FIG. 10).

Figure 10:
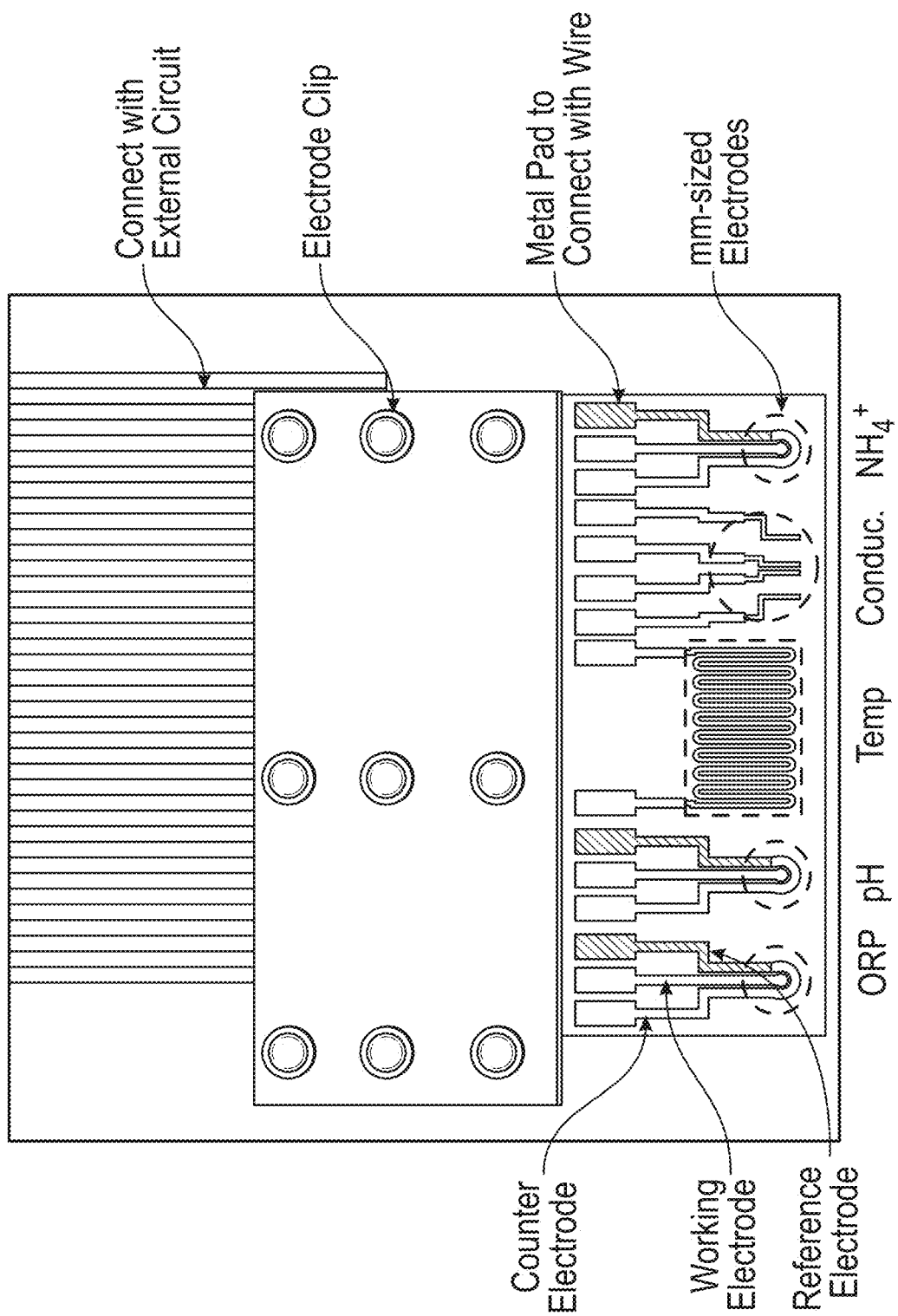
FIG. 10 shows an exemplary MEA setup with an external circuit and a data logging system.

For the ORP, pH and $NH_4^+$ sensors, three-electrode systems include the same pattern gold-based working and counter electrodes, and silver-based reference electrodes (FIG. 10). Then, the working electrode of the pH sensor can be modified through the deposition of $Ir_2O_3$, and the working electrode of the $NH_4^+$ sensor can be modified with a coating of polyaniline. The temperature sensor can be made by a zip-shape gold-based resistance and conductivity sensor that includes four gold-based electrodes as a capacitor (FIG. 10).

The uniquely designed MEAs are more accurate and sensitive, since the electrochemical signals can be immediately and fully collected by the adjacent counter electrode (FIG. 10). This is very different from the existing electrodes which need a separated reference/counter electrode. The ink-jet printed MEA sensors are low cost (e.g., $0.2 per sensor, mainly gold/silver ink cost) and are easy to mass fabricate. The precise alignment of each electrode on the film makes the MEA individually addressable, which substantially eases the in situ measurement in the field. The electrochemical signals of the MEAs can be recorded using a multiple-channel data-logging system. For example, the $NH_4^+$ concentration can be measured using current; the pH and the ORP can be measured using potential; the conductivity can be measured using capacitance; and the temperature can be measured using resistance.

Figure 11B:
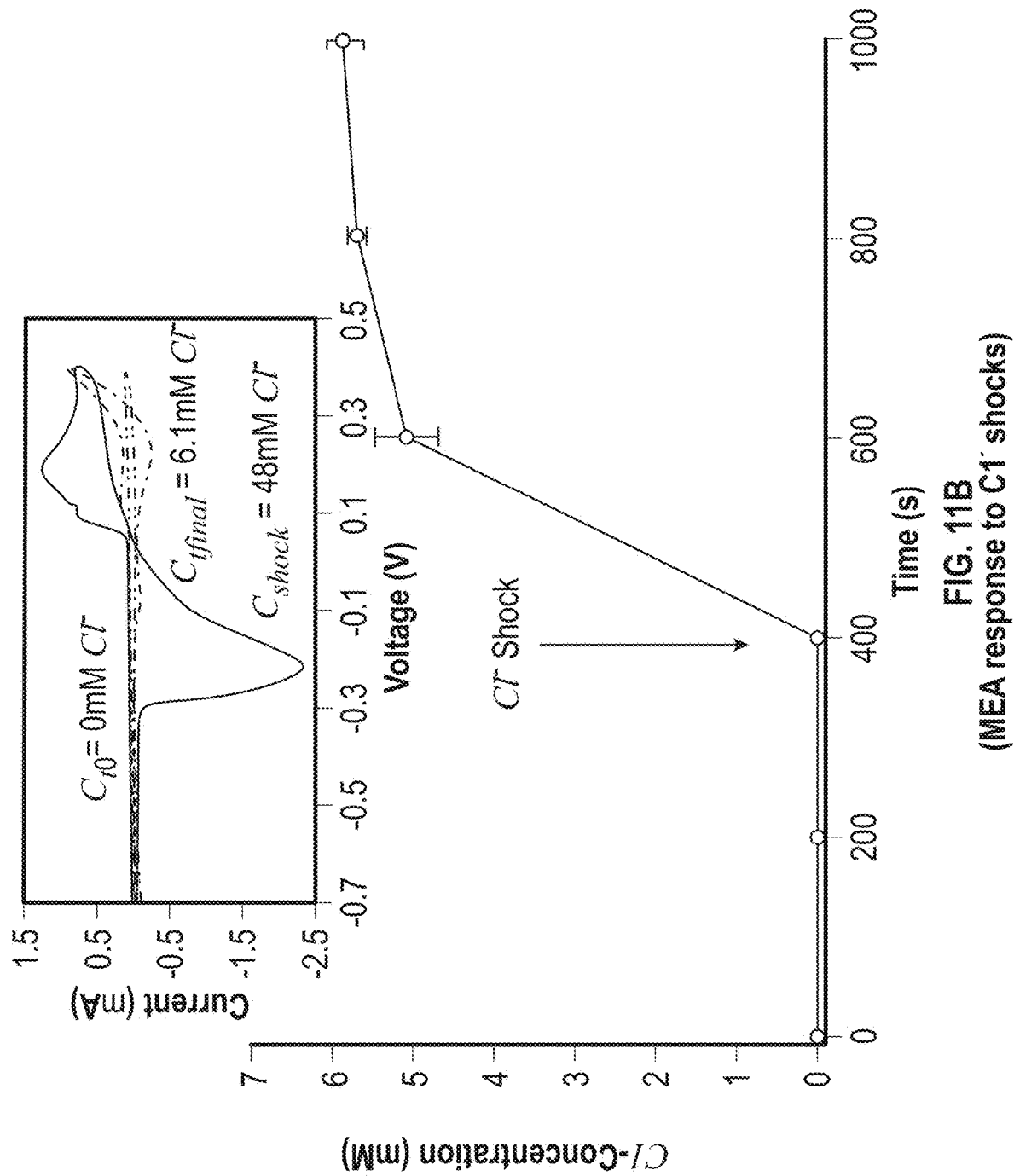
FIG. 11B shows MEA response to shocks.
Figure 11C:
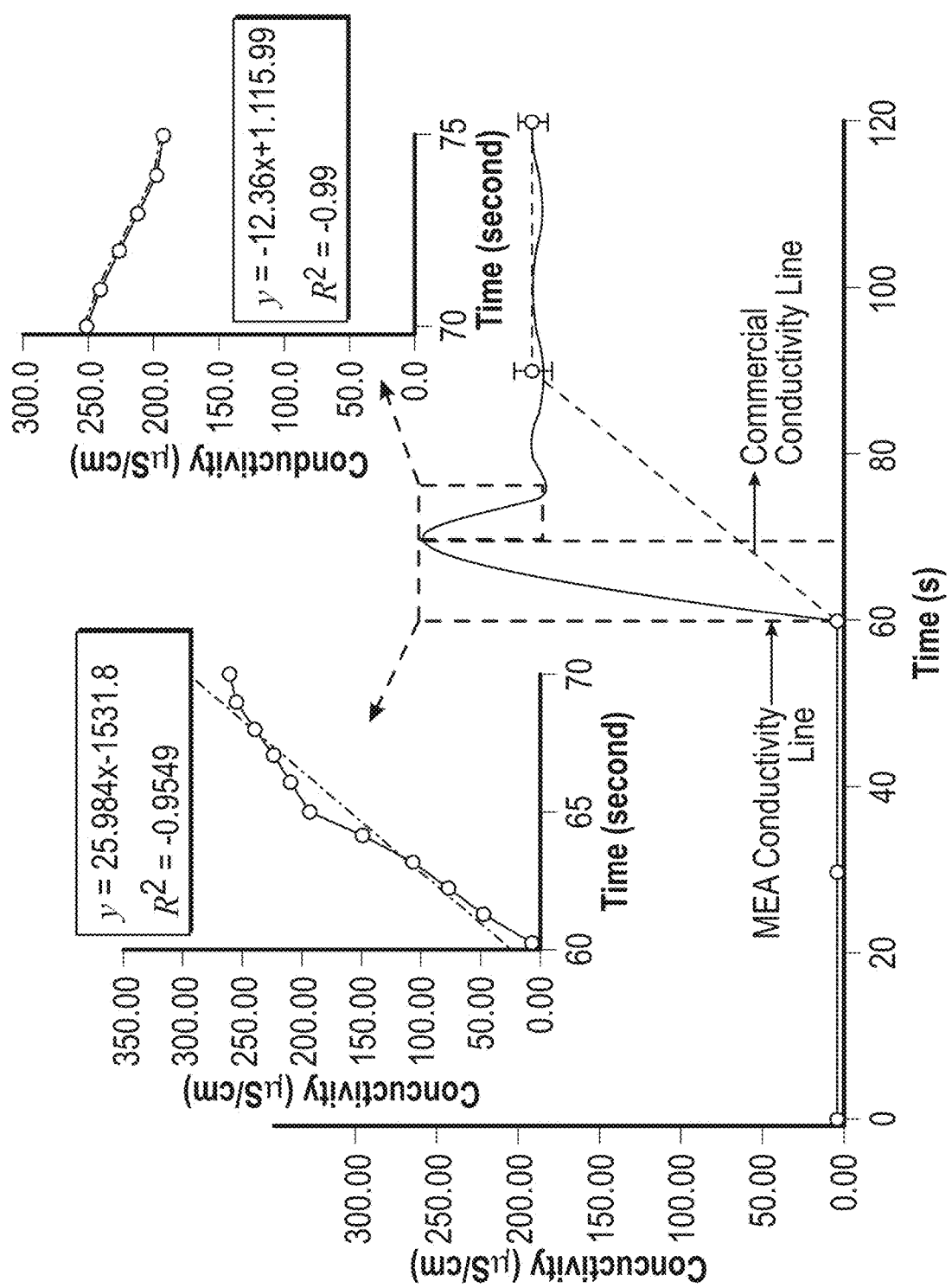
FIG. 11C shows MEA response to salt (NaCl) shocks, and compared with commercial conductivity sensors, showing high sensitivity and fast response time.

Each exemplary type of sensor of the MEA assembly can be calibrated to establish an accurate correlation between electrochemical signals and the targeted parameters. The calibration has been conducted in water solutions that well represent typical wastewater, with ORP of −350−+300 mV, pH of 2 to 10, temperature of 10 to 50° C., conductivity (indicating dissolved solid content) of 1500 to 3000 μS/cm, and $NH_4^+$ 20 to 100 mg/L. Each type of sensor showed high accuracy between electrochemical signals and the targeted parameters with $R^2$ values higher than 99% (FIG. 5). Besides calibration, a shock test was conducted by rapidly changing water temperature and conductivity to simulate water system malfunction (e.g., temperature fluctuation and fatty acid accumulation in AD systems). The MEA sensors showed the real-time signal change with the shock (FIG. 11A, only showing conductivity and temperature response), indicating an excellent capacity of capturing the shock of impaired water quality. FIG. 11B shows MEA response to $Cl^-$ shock and FIG. 11C shows MEA response to salt (NaCl) shocks, and compared with commercial conductivity sensors, showing high sensitivity and fast response time.

It should be noted that mm-sized electrodes on the MEA are not limited to these five parameters. Each electrode can be easily modified using surface coating and electrochemical deposition to monitor a wide range of other parameters (e.g., toxic metal ions, pesticide, salt, and nutrients, etc.).

Example 2

Four types of MEA sensors targeting critical water-quality parameters (two physical parameters: temperature and conductivity; two chemical parameters: DO and pH) were fabricated using IPT technology. Precise patterning of multiple mm-sized electrodes on a flexible plastic film was achieved. The electrodes are adapted for easy installation inside treatment systems to rapidly profile multiple parameters, and thus elucidate the heterogeneous status of systems for decoding the "black box" and executing proactive control strategies.

Four tasks were undertaken and completed in connection with this Example 2. First, physical MEAs (temperature and conductivity) were fabricated and then calibrated using standard linearity models by measuring the resistance of MEAs. Second, chemical MEAs (pH and DO) were fabricated and then calibrated using the electrochemical method to establish the standard linearity model between the MEA signals with pH and/or DO. Third, the sensitivity and accuracy of each of the MEA types were validated in shock tests simulating water/wastewater processes. The response time of each MEA to shocks was examined and compared with commercial probes. Shock models were developed based on the real-time MEA data. Finally, the long-term stability of MEAs was examined by inserting MEAs into wastewater and activated sludge for over 1-month period.

1. Materials and Methods a. Sensor Material Preparation

Kapton FPC film (thickness: 127 μm, American Durafilm) was washed with deionized water (DI water) and ethanol prior to the usage as the sensor substrate. Compared with a rigid silicon wafer, the flexible Kapton film had the distinct advantages of easy deployment/replacement, durable structure and high robustness. Gold (III) chloride trihydrate, 1-dodecanethiol, tetraoctylammonium bromide, sodium borohydride, N-hydroxysulfosuccinimide, 1-ethyl-3-[3-dimethylaminopropyl], and carbodiimide hydrochloride (Sigma-Aldrich Co.) were used to synthesize the gold ink (Dodecane thiol-protected gold nanoparticles) for MEA working electrodes. Silver nanoparticles ink (SunTronic® Silver, Sigma-Aldrich Co.) was used as the silver ink for MEA reference electrodes. Poly (amic acid, Sigma-Aldrich Co.) ink was used as the waterproof layer printed on the top layer of MEAs and was prepared by diluting 10% (m/m) poly (amic acid) solution in highly pure N-methyl-2-pyrrolidone (NMP) to 1% (m/m). Iridium (IV) chloride, hydrogen peroxide and potassium oxalate (Fisher Scientific Co.) were prepared for iridium tetrachloride solution for pH working electrode. Phosphate-buffered saline (PBS) solution was prepared by mixing sodium hydrogen phosphate, sodium chloride, potassium chloride and potassium dihydrogen phosphate (Fisher Scientific Co.) in the DI water, and was used for the stabilizing solution for the pH working electrodes.

A Dimatix Materials Printer (ModelDMP-2800, FUJIFILM Dimatix, Inc. Santa Clara, Calif.) was used for printing MEA sensors. The liquid crystal polymer printer cartridges (Model DMCLCP-11610, Dimatix 10 pL) were used for all the inks (gold, silver and poly amic acid inks). The printing pattern was designed using the AutoCAD program and transferred by the LinkCAD program. Each pattern of a MEA was printed with a 15 μm space between the ink drops by using a customized printing waveform, with each pattern being printed using two jets for facile detection of any potential clog.

b. MEA Printing Pattern Design

Figure 12A:
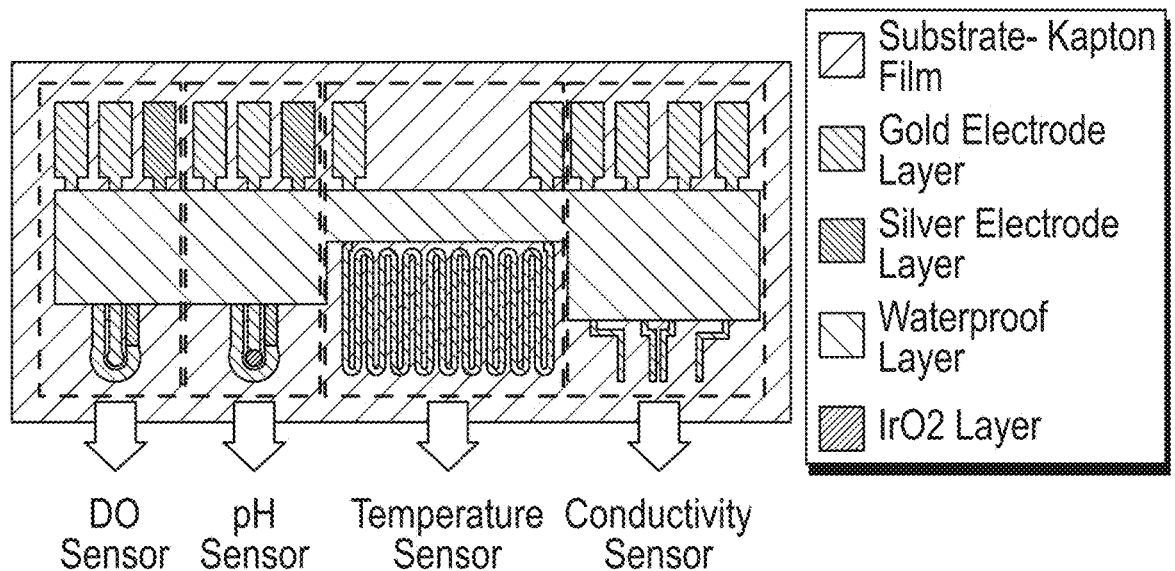
FIGS. 12A and 12B are schematic diagrams of exemplary DO, pH, temperature and conductivity MEA sensors and layers for MEA of the present disclosure.
Figure 12B:
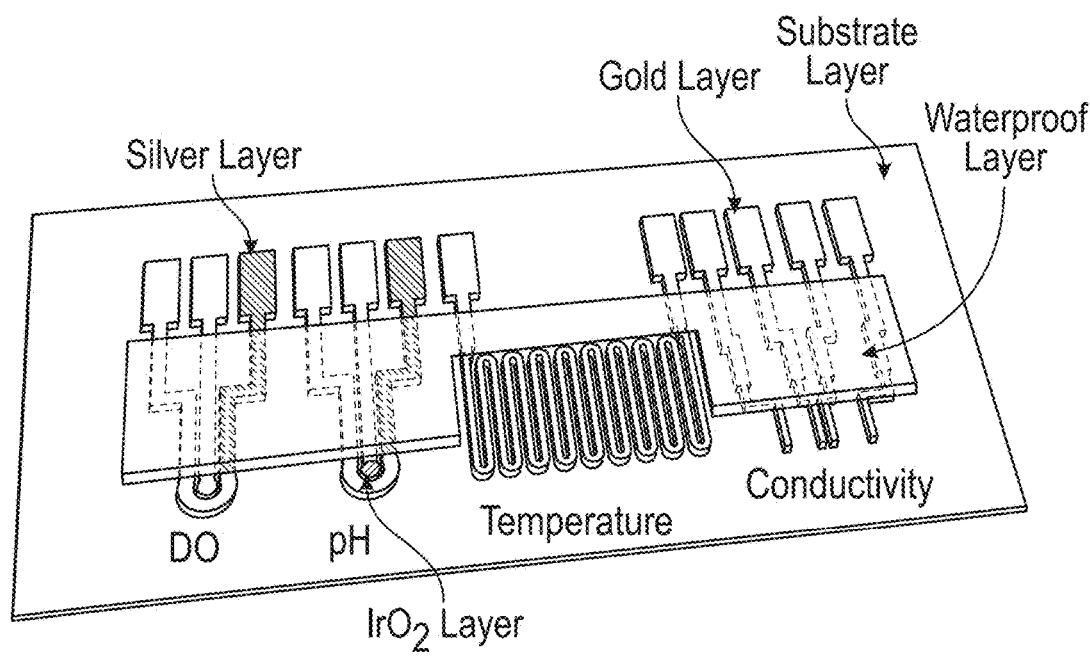

With reference to FIGS. 12A and 12B, a typical MEA pattern consisted of DO sensor, pH sensor, temperature sensor and conductivity sensor (from left to right). Each MEA sensor had three layers: the substrate layer (Kapton film), the electrode layer and the water-proof layer. Each electrode layer was printed using specific type of metal inks (e.g., gold ink for the working and counter electrodes, and silver ink for the reference electrodes). Specifically, the pH and DO sensors possessed the three-electrode configuration, including one working electrode (gold ink), one counting electrode (gold ink) and one reference electrode (silver ink). For the pH sensor, the working electrode was modified using iridium oxide that was widely used for pH detection after the gold the silver layers were printed on the film. The temperature sensor printed solely using the gold ink was a resistance thermometer in which the change of resistance was directly associated with temperature. The conductivity sensor printed solely using the gold ink was a four-electrode sensor to measure the resistivity of water solution, which directly reflected the total amount of dissolved salts in a water solution.

c. MEA Fabrication Protocols

Before printing MEAs, a clean Kapton polyimide film (FPC, size: 22×28 cm) was placed in the Dimatix printer, heated to 35° C. and secured using a platen vacuum. The gold electrode layer, the silver electrode layer and the waterproof layer were printed sequentially on the Kapton substrate films following the same process. During the printing process, the gold nanoparticle ink cartridge in the Dimatix printer was visually checked using a high-speed drop camera to ensure the consistent ink droplet formation. The printer was aligned with the Kapton film, and the patterning program was set to allow for printing multiple sensor arrays simultaneously, with a space of 3-5 cm between each sensor array. Specifically, the gold nanoparticle ink was first printed onto the film, followed by heating to 200° C. for 3 min or until the color of the gold layer lightened which indicated the loss of the dodecane thiol layer and the decrease in the resistance of the MEA gold layer. The film was then rinsed with the DI water and aligned before printing the silver layer, and then the film was heated to 150° C. for 10 min or until the color of the silver layer lightened. Finally, the poly (amic acid) layer was printed on the top of the silver layer and the film was heated to 200° C. for 30 min for imidization of the poly (amic acid) solution.

The MEAs were placed in 0.18 M sulfuric acid ($H_2SO_4$, Fisher Scientific CO, connected to a potentiostat, and cycled from −0.2 V to +1.5 V vs. SCE to clean the electrodes. After the cleaning, temperature sensors, conductivity sensors and DO sensors did not need further modification, while the pH sensors were modified by electrochemically coating an iridium oxide ($IrO_x$) layer on the working electrode using cyclic voltammetry (CV, Gamry Reference 600) at a scanning potential from −2.0V to +0.8V, and the scan rate of 100 mV/s for 12 cycles. Afterwards, all MEA sensors were dipped into 1 mL PBS buffer solution (pH 7.41) for 2 days to stabilize and reduce the signal drift in water solution. Finally, MEA sensors were connected with the copper wire and coated with the sealant silicone (Dow Corning 734 Flowable Sealant) as the waterproof layer on the electrode connection pads. The mm-sized electrodes uncovered by the waterproof layer were directly exposed to water solution.

d. MEA Calibration

Each type of MEAs was calibrated at room temperature (20° C.) with four-time duplication. For the temperature MEA, the working electrode and counter/reference electrodes were individually connected with a potentiostat (Gamry Reference 600). The MEA was immersed into the DI water in a beaker on the heater (Thermolyne 1000 hotplate). A commercial temperature sensor (Thermo Scientific Orion 3 star conductivity meter) was put into the beaker near the MEA as the control measurement. When the water solution started heating from 20° C. to 50° C. (simulating adversely high wastewater temperature) and then cooled to 4° C. (simulating cold nature water), the temperature MEAs were applied with the current-time program at a setting potential 0.2V, and the MEA readings were recorded each 100 seconds for 2300 seconds.

For the conductivity MEA, two outer electrodes were connected with a direct current (DC) power supply (GWinstek SFG 1013) that provided the stable current, while the two inner electrodes were connected with the working electrode and counter/reference electrodes of the potentiostat. The conductivity (from 197 μs/cm to 152 ms/cm) of nineteen sample solutions made by dissolving different amounts of sodium chloride (NaCl, Fisher Scientific Co.) into the DI water was measured by the commercial conductivity meter (Thermo Scientific Orion 3 star conductivity meter). The conductivity MEAs were applied with a 60-second open potential program for each sample during calibration. The data used for the conductivity calibration was the average of the 60-second data.

For the DO MEA, three electrodes were individually connected with the working electrode, the counter electrode and the reference electrode of the potentiostat. Six solutions with different DO concentrations (0.2 to 8.91 mg/L) were made by dissolving different amounts of sodium sulfite ($Na_2SO_3$, Fisher Scientific Co.) into the fully aerated solution. The DO MEAs were applied using cyclic voltammetry (CV) at a scanning potential from −0.9V to 0V, and the scan rate of 200 mV/s for 12 cycles, and were validated with a commercial DO meter (Thermo Scientific Orion 3 star DO meter).

For the pH MEA, three electrodes were individually connected with the working electrode, the counter electrode and the reference electrode of the potentiostat. Six pH solutions (pH: 2, 3, 5, 6, 8 and 9) were prepared using hydrochloric acid (HCl), sodium hydroxide (NaOH), Sodium chloride (NaCl), potassium hydrogen phthalate, phosphate, and Tris buffer solution (Fisher Science, Co.). The pH MEAs were applied using a 100-second potential-time measurement for each sample, and validated using a commercial pH sensor (Thermo Scientific Orion 3 star pH meter).

e. MEA Lab Shock Tests

MEA lab shock tests were conducted to examine the accuracy and the response time of MEAs during the transient shock period. Each MEA shock test was duplicated for four times.

For the MEAs lab shock tests, the MEAs and the commercial sensor were put into a beaker with the original solution (500 mL). The connection between the electrodes of the MEAs (temperature, conductivity, DO and pH) and the potentiostat was the same as the calibration process. The shock solution (50 mL) was injected into the original solution 60 seconds after the potentiostat electrochemical program started. For the temperature shock, the shock solution (hot DI water) increased the temperature from room temperature (20° C.) to 50° C. using the heating plate. The temperature observed by the commercial temperature sensor was recorded each 30 seconds after the I-t program of the potentiostat started.

For the conductivity shock, shock solution (1000 mg/L NaCl) was injected into the original solution (2 mg/L NaCl). The conductivity observed by the commercial conductivity sensor was recorded each 30 seconds after the resistance measurement program of the potentiostat started.

For the DO shock, oxygen gas was first pumped into the original solution to reach the saturated DO (about 8.91 mg/L). The shock solution was the DI water dissolved with sodium sulfite ($Na_2SO_3$, Fisher Science, Co.) as the oxygen scavenger for one hour to reduce the DO to 0.2 mg/L, which was verified by the commercial DO sensor. The DO shock solution was rapidly injected into the fully aerated solution, during which the DO was recorded using the DO MEA and compared with the commercial probe.

For the pH shock, the shock solution (0.01 M HCl solution at pH of 2.09) was rapidly injected into the original solution (20° C. DI water at pH of 7.08). The pH measured using the pH MEAs was recorded each 30 seconds after the potential-time program of the potentiostat started, and compared with the commercial pH sensor.

f. Microscopic Observation of MEAs Immersed into Wastewater and Sludge

Long term stability of MEA sensors is important for monitoring of wastewater quality. Electrode fouling caused by the attachment of biofilms and particles is an inevitable phenomenon that would affect the monitoring accuracy and signal sensitivity in long run. MEA stability was examined within 4-week operational period. Multiple pieces of MEAs were immersed into wastewater (chemical oxygen demand (COD): 250-350 mg $L^{-1}$ and biological oxygen demand (BOD): 100-300 mg $L^{-1}$) and waste sludge individually that were collected from University of Connecticut Wastewater Treatment Plant (WWTP). Every week, a MEA sample was taken from the wastewater and sludge, respectively, and gently rinsed by DI water for 5 seconds before the surface observation using a digital microscope (Nikon Labophot). Because the resistance of MEAs can directly demonstrate the electrode fouling status, the resistance of each MEA sensors was used as an indicator of the whole MEA and measured at ambient temperature (25° C.) using a digital multimeter weekly for 4 weeks to elucidate the electrode fouling influence. In addition, the accuracy of the temperature, conductivity, DO and pH MEAs was validated within 4-week operational period.

2. Results and Discussion a. Calibration of Physical MEA Sensors (Temperature and Conductivity).

Figure 13A:
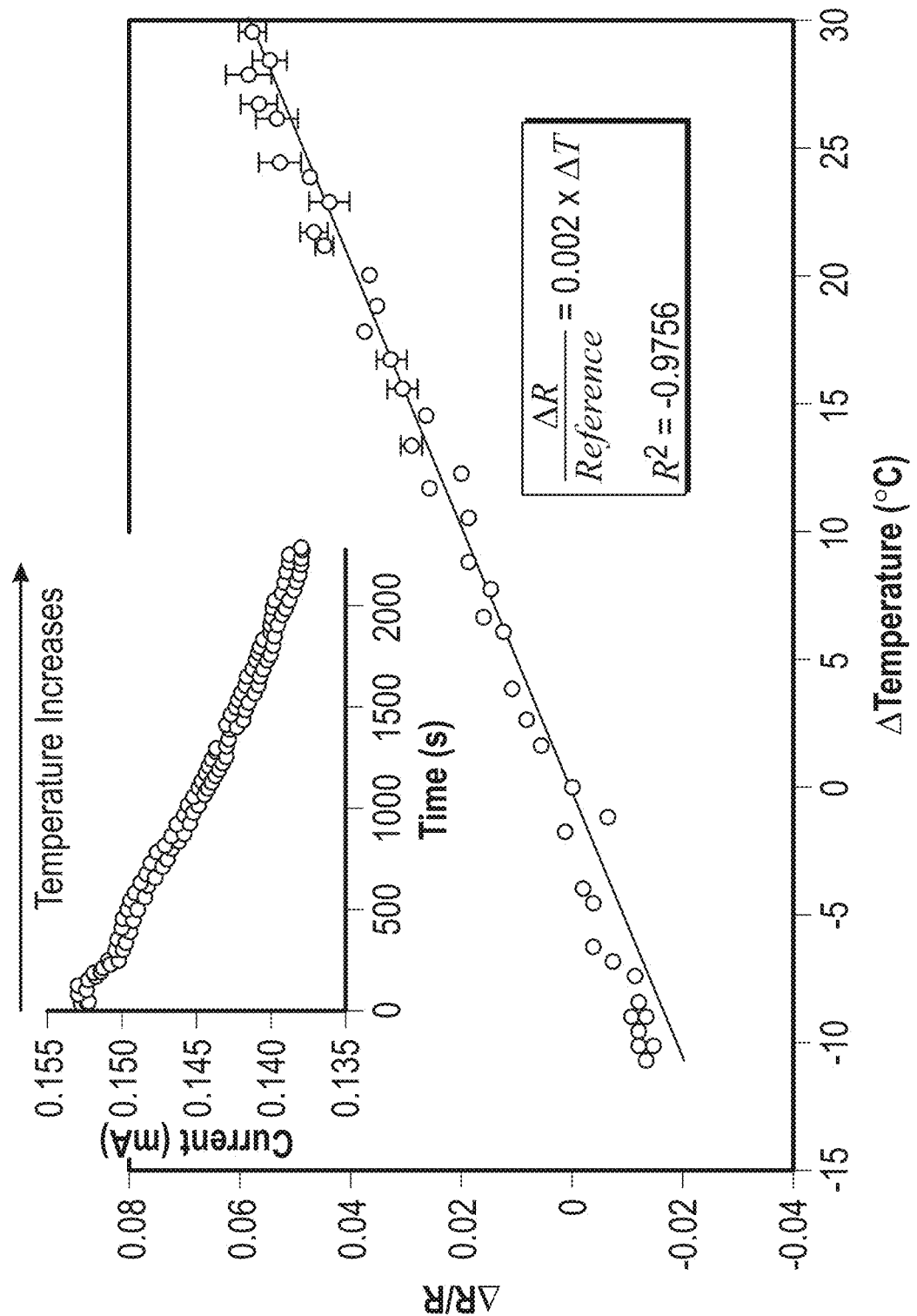
FIG. 13A is an MEA calibration curve using the linearity model of the temperature MEA resistance ($\Omega$) vs. temperature (° C.)

Two physical MEAs (temperature and conductivity) were calibrated, in which the targeted water quality parameters did not react with MEAs but only caused the variation of resistances of MEAs under the fixed potential. The results showed that the current of the temperature MEAs decreased over time with the increase in the temperature of the water solution (FIG. 13A). At the fixed potential set by the potentiostat program, the resistance of the temperature MEAs (R=V/I) decreased at high temperature, since the metal conductor used in this study, dodecane thiol-protected gold nanoparticles (AuNPs) has a positive temperature coefficient. The temperature MEAs were designed as the standard resistance temperature detectors (RTDs), which directly correlated the resistance with temperature (Equation 1).

$$\Delta R = \alpha R_r \Delta T \qquad (1)$$

where $\Delta R$ is the difference between the actual resistance and the reference resistance ($\Omega$).

$\alpha$ is the temperature coefficient of resistance (TCR) (($\Omega/\Omega$)/° C.), which is also regarded as the sensitivity of a temperature sensor.

$R_r$, the reference resistance, is the resistance of the temperature MEA at 20° C. ($\Omega$).

$\Delta T$ is the difference between the actual temperature and the reference temperature (20° C.) (° C.).

The sensitivity (α) of the temperature MEA was 0.002 (FIG. 13A), indicating that the resistance hardly changed with the variations in temperature. TCR (α in this model, 0.002) was lower than the pure gold (0.003715 at 20° C.), since the gold ink used in this study was AuNPs and decreased the TCR in the model. Compared with the traditional temperature micro-sensors fabricated using PCVD, the temperature MEAs showed similar sensitivity (0.0025-0.0048).

Figure 13B:
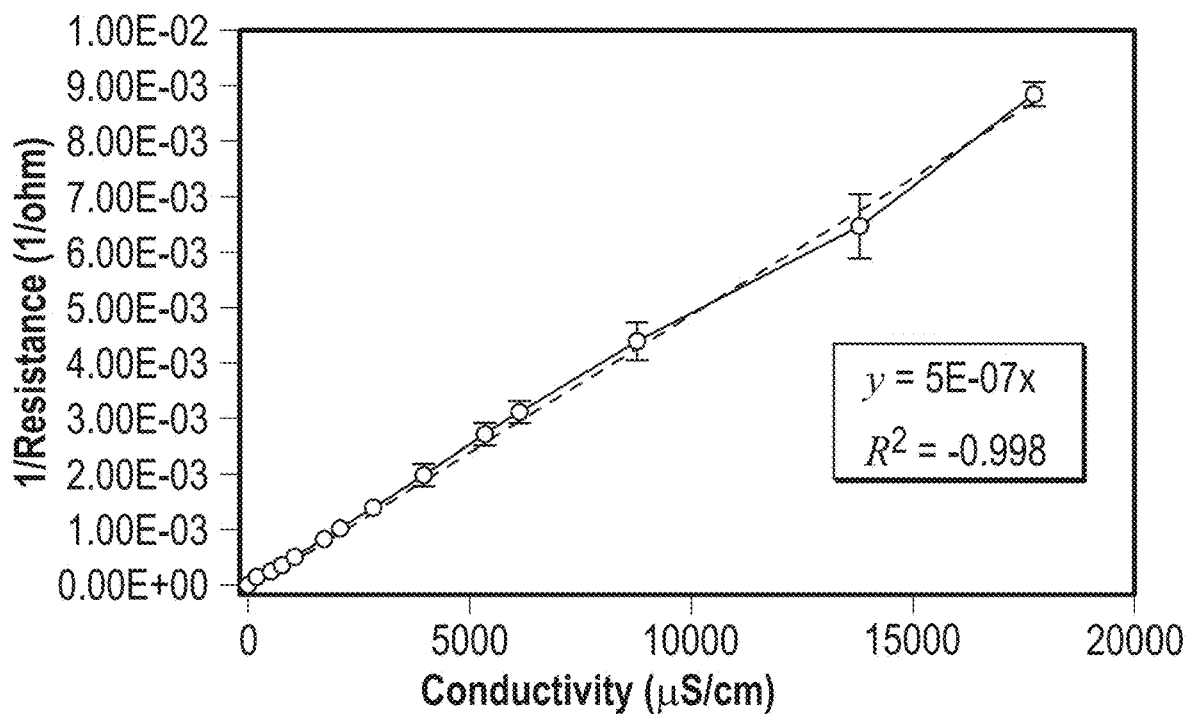
FIG. 13B is an MEA calibration curve using the linearity model of the conductivity MEA resistance ($\Omega$) vs. calibration conductivity ($\mu$s/cm)

The conductivity MEAs indicated the capacity of a water solution to conduct an electric current between two electrodes, which was highly related with the ionic strength. By increasing NaCl concentration, the ionic strength of the water solution increased and led to higher conductivity (FIG. 13B). The resistance between the two electrodes can be calculated by the average voltage between the two electrodes at the stable current during 100 seconds. The relationship between the conductivity of the water solution and the reciprocal of the resistance between two electrodes of the MEAs was described in Equation 2.

$$C = K(1/R) \quad (2)$$

where
R is the resistance between two electrodes (Ω);
C is the conductivity of a solution (S/cm);
K, the cell constant, was the ratio of the distance between the electrodes to the effective area of the electrodes (Ω·S/cm).

The $R^2$ value (0.9982) indicated a high degree of linearity between the resistance of the conductivity MEAs and the solution conductivity (FIG. 13B). The conductivity MEA has a better response time (less to 0.1 second) over the commercial conductivity sensors (about 10-30 seconds), with similar R square value (>0.95), since the four-electrode structure efficiently reduced the effects of polarization and increased the accuracy compared with the two-electrode conductivity structure. Furthermore, the miniature size (<1 mm) of the MEA sensors minimized the impact of the sensor to the solution compared with traditional conductivity sensors (>100 mm). Due to the close association between conductivity and temperature, the integration of conductivity sensors and temperature sensors on the same film can achieve auto-correction at different temperatures.

b. Calibration of Chemical MEA Sensors (DO and pH).

Two chemical MEAs (DO and pH) were calibrated, in which the working electrodes of MEAs reacted with the targeted water quality parameters and caused the current/potential variation. The cyclic voltammetry (CV) model of the DO MEA was described according to Equation 3 below.

$$\frac{i}{i_0} = \left(1 - \frac{i}{i_{1,c}}\right) e^{-\alpha n f \eta} - \left(1 - \frac{i}{i_{1,a}}\right) e^{(1-\alpha)nf\eta} \quad (3)$$

where
$i_0$ is the exchange current,
α is the transfer coefficient;
n is the number of electrons;
f is the ratio of Faraday's constant to that of the ideal gas constant and temperature;
η is the over-potential, and
$i_{1,c}$ and $i_{1,a}$ are the diffusion limited cathodic and anodic currents, respectively.

Figure 14A:
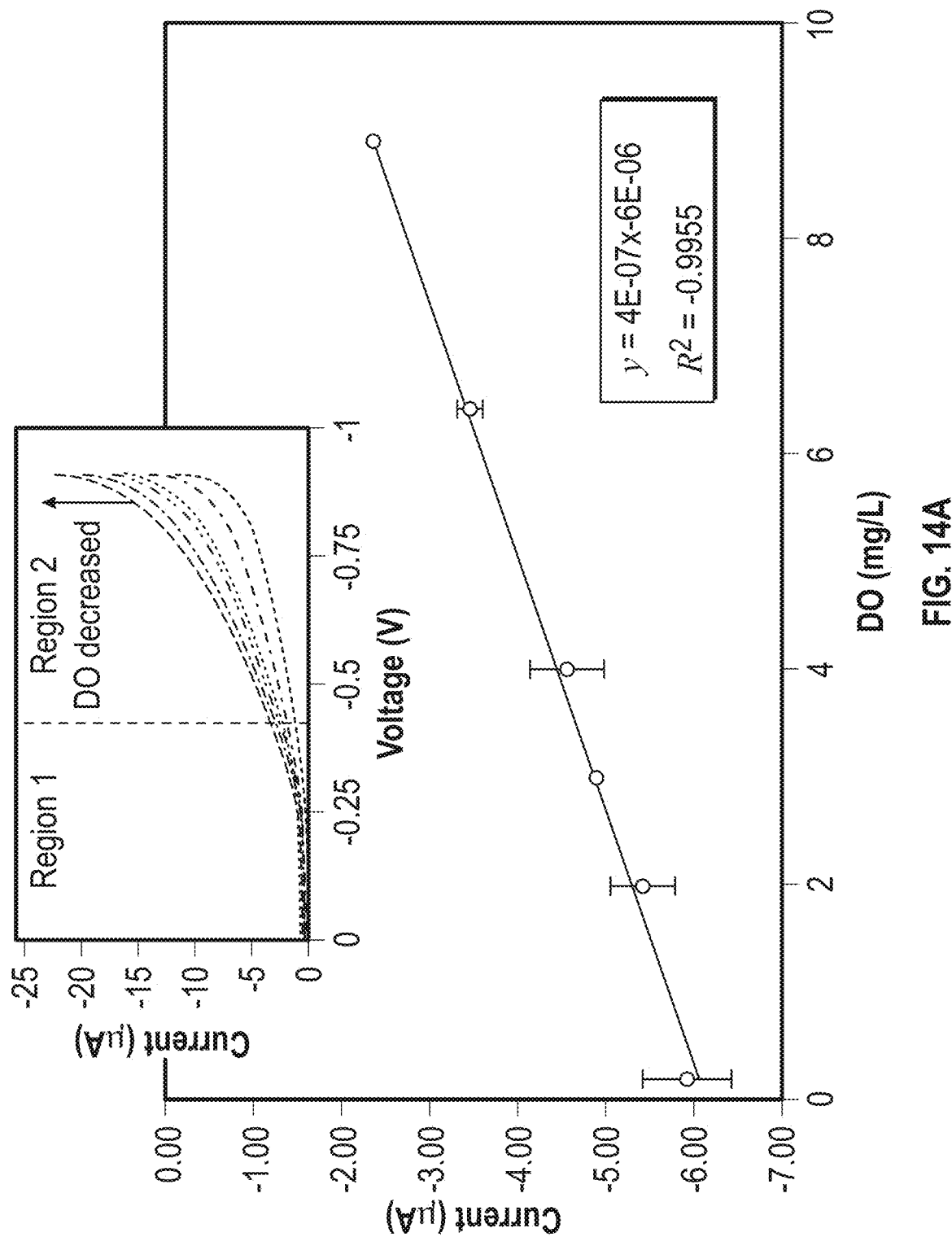
FIG. 14A shows chemical MEA calibration based on the average value from four-time duplication tests using the linearity model of the DO MEA current ($\mu$A) vs. DO (mg/L)

The model described the two regions: the kinetic control region with low bias (Region 1) and the diffusion control region with high bias (Region 2). The current was proportional to the DO concentration in the Region 2 (FIG. 14A), and the current value used for the model was set as the current at the potential (0.75 V) in Region 2. The high $R^2$ value (0.9955) reflected an excellent linearity between the current and the DO concentration (FIG. 14A). Previous study found that the accuracy of DO sensors was associated with the size of the working microelectrodes (10-20 mm) and the space between the working electrode and the reference electrode [G. W. McLaughlin, K. Braden, B. Franc and G. T. Kovacs, Microfabricated solid-state dissolved oxygen sensor, Sensors and Actuators B: Chemical 83.1 (2002): 138-148; R. D. C. S. Luz, F. S. Damos, A. A. Tanaka and L. T. Kubota, Dissolved oxygen sensor based on cobalt tetrasulphonated phthalocyanine immobilized in poly-1-lysine film onto glassy carbon electrode, Sensors and Actuators B: Chemical 114.2 (2006): 1019-1027]. The higher $R^2$ value (0.9955) in this study was a bit higher than that (0.95) in the previous study, since the working electrode of the DO MEA was less than 8 mm and the space between the working electrode and the reference electrode was only 1 mm, which reduced the electron transfer resistance and enhanced the sensor accuracy.

Figure 14B:
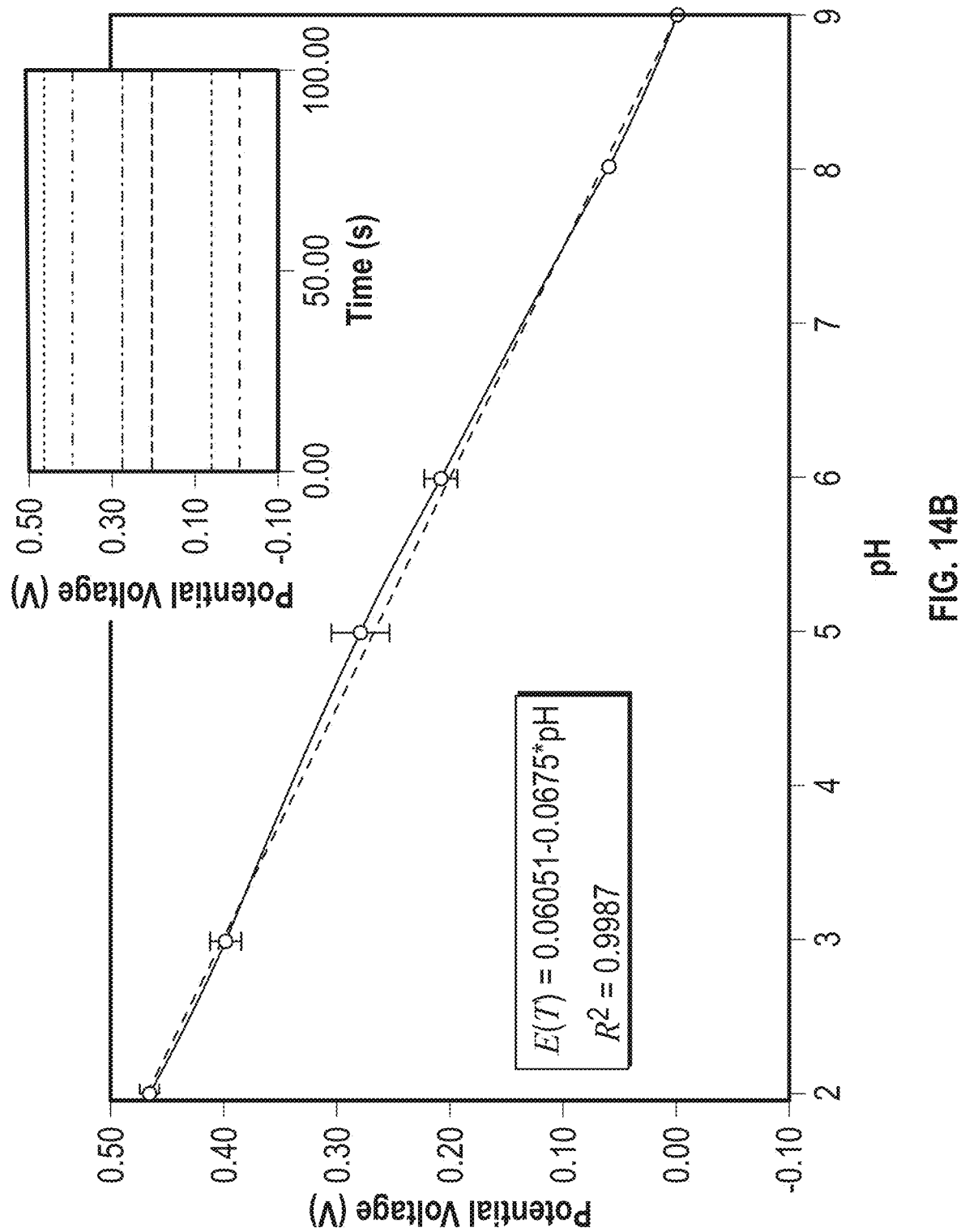
FIG. 14B shows pH MEA potential (V) vs. pH.

The potential of the pH sensor decreased with pH increasing (FIG. 14B). The linearity relationship between the potential and the pH was described as the Nernst Equation (Equation 4).

$$E(T) = E°(T) + \frac{2.303\, R*T}{n*F} *\text{pH} \quad (4)$$

where
E (T) is the potential of the pH temperature;
E°(T) is the constant standard potential (mV) at temperature T (Kelvin);
R is the molar gas constant (8.3144 J mol-1 K-1);
F is the Faraday constant (96485 C mol$^{-1}$);
T is the temperature (Kelvin); n is the charge of the ion;
The entire term (2.303RT/nF) is the slope of the Nernst Equation.

Based on the Faraday's law, the voltage of all the V-t curves (pH: 2, 3, 5, 6, 8 and 9) dropped slowly over time. The 80$^{th}$-second voltage was regarded as the stable voltage, since it only drifted 0.19 mV within 20 seconds (from 80$^{th}$ second to 100$^{th}$ second), and thus being used as the E (T) in this study. High $R^2$ value (0.9987) showed an excellent linearity between pH and the MEA potential (FIG. 14B). The slope of (−67.5±0.5 mV/pH) (FIG. 14B) was slightly lower than that (70 mV/pH) in previous studies, since the calibration temperature was 20° C. in this study rather than 25° C.

Furthermore, previous studies found that the drift was around 2-47 mV (1-20 μV/second) after the conditioning period (10 min), while the drift of the pH MEA in this study (pH 8) was about 0.19 mV in 20 seconds (10 μV/second) after the conditioning period (80 sec.). The shorter conditioning period was caused by the smaller size of the pH MEA (mm-sized) than the traditional pH sensor (cm-sized) that increased the stability of the pH MEA. However, the reference electrode of the pH MEA was printed using silver (Ag) nanoparticles, which had a lower potential stability than silver chloride (AgCl) used in traditional pH sensors. Therefore, it is contemplated that modification to the reference electrode using AgCl might further increase the stability of the pH MEAs.

Figure 15A:
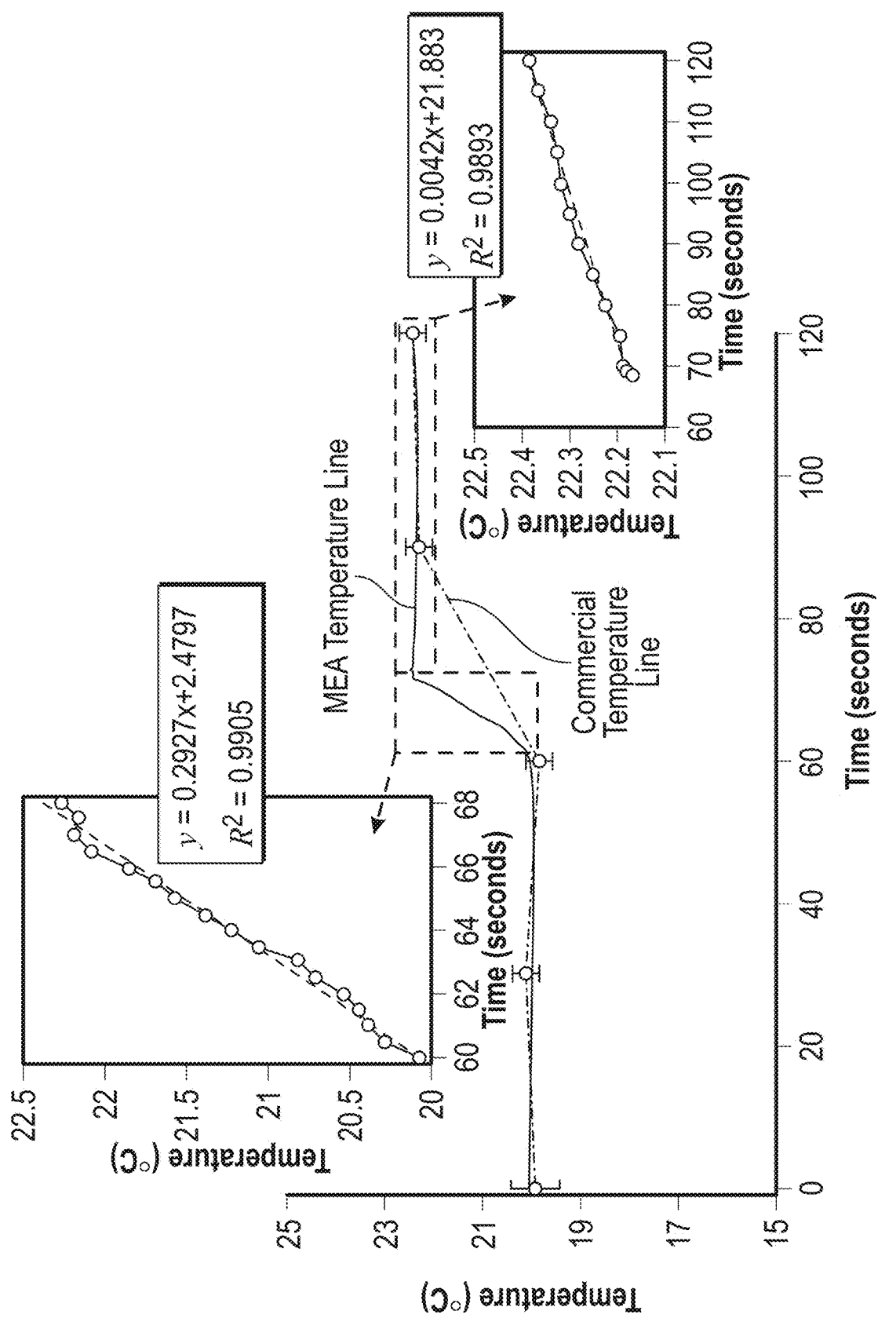
FIG. 15A shows the response of exemplary MEA sensors and commercial probes to the shock of temperature.

Similar to the conductivity MEA, the pH sensor should be real-time corrected with temperature to obtain a high accuracy of pH measurement. The slope (2.303RT/nF) indicated that temperature significantly influenced the sensor open potential and the pH value. The influence factor of the temperature was set as 0.06 pH1° C., meaning that pH readings would change when the temperature of the water solution became different from the reference temperature (20° C.). Integrating pH sensor and temperature sensor in a MEA would effectively eliminate the potential temperature error by real-time auto adjusting the slope.

c. Sensitivity and Accuracy of MEAs Under Shocks of Temperature and Conductivity in Water Solutions The sensitivity and accuracy of MEAs were examined in a water solution under the shocks of each parameter. The temperature of the solution was stable at 20° C. before the shock tests (FIG. 15A). When the shock input (50 mL solution of 50° C.) occurred on the $60^{th}$ second, the temperature increased rapidly within next 5-10 seconds and reached 22° C. on $80^{th}$ second. Finally the reading of the temperature MEA stabilized at 22.4° C. (FIG. 15A), which was almost the same as the theoretic temperature of the final mixture solution (22.73° C.). The accuracy of the temperature MEA was validated using a commercial temperature sensor. The ratio of the estimated temperature (based on the temperature MEA) to the actual temperature (based on the commercial temperature sensor) ranged between 98.75% and 101.25%, demonstrating that the superb accuracy of the temperature MEA (>100±1.25%). In addition, the I-t program recorded the current every 0.1 seconds and caught the current change simultaneously under the shock.

The rapid response time of the temperature MEA was much shorter than that of commercial temperature sensors (about 5-20 seconds), and enabled the capture of the transient shock (lasting less than 5-10 seconds) (FIG. 15A). The temperature shock pattern consisted of three stages: the stable stage (before the shock), the fast increase stage (during the shock) and the slow increase stage (after the shock) (FIG. 15A). At the fast increase stage and the slow increase stage, the temperature increase was linearly related ($R^2$>0.98), and the temperature increase rate of the fast increase stage (0.2927° C./second) was about 70 times as that of the slow increase stage (0.0042° C./second) (FIG. 15A). The fast increase stage was caused by the direct heat transfer from the high temperature shock solution to the low temperature original solution, while the slow increase stage was caused by the partial heat diffusion in the mixture solution the addition of the shock solution.

For the conductivity shock, the original solution (2 mg/L NaCl solution, 500 mL) had the conductivity of 4.4 µS/cm to simulate the clean water sources (conductivity lower than 200 µS/cm). The shock input (1000 mg/L NaCl solution, 50 mL) had the conductivity of 1980 µS/cm to simulate the saline wastewater, which was verified by the commercial conductivity sensor. According to relationship between the NaCl concentration and the conductivity, the final mixture solution with the NaCl concentration of 92.73 mg/L had the calculated conductivity of 195 µS/cm, which was close to the measurement results of the conductivity MEA (191 µS/cm, FIG. 15B). The ratio of the estimated conductivity (based on the conductivity MEA model and temperature correction) to the actual conductivity (based on the conductivity commercial sensor) ranged between 98.50% and 101.50%, demonstrating that the superb accuracy of the conductivity MEA (>100±1.50%).

Figure 15B:
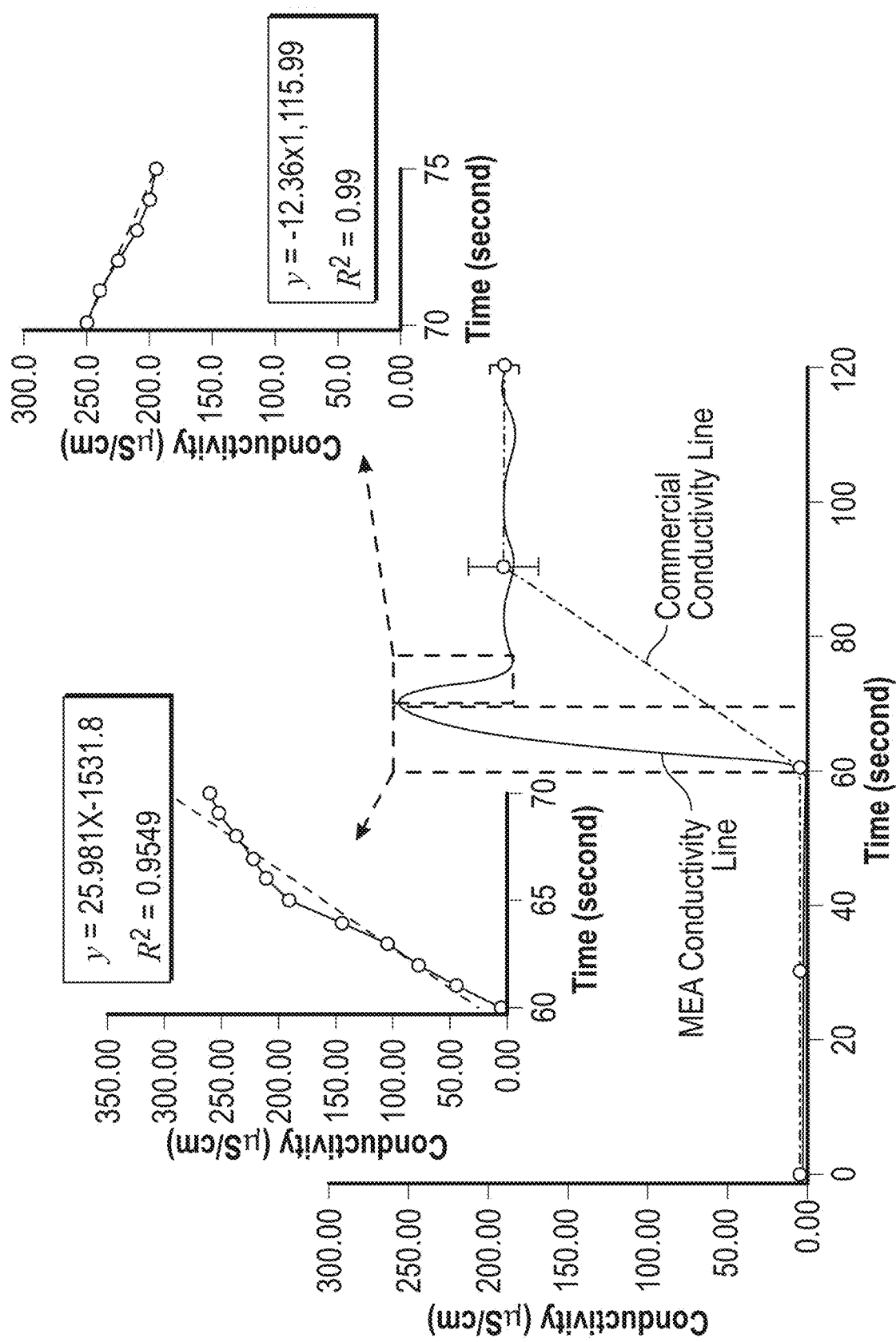
FIG. 15B shows the response of exemplary MEA sensors and commercial probes to the shock of conductivity.
Figure 15C:
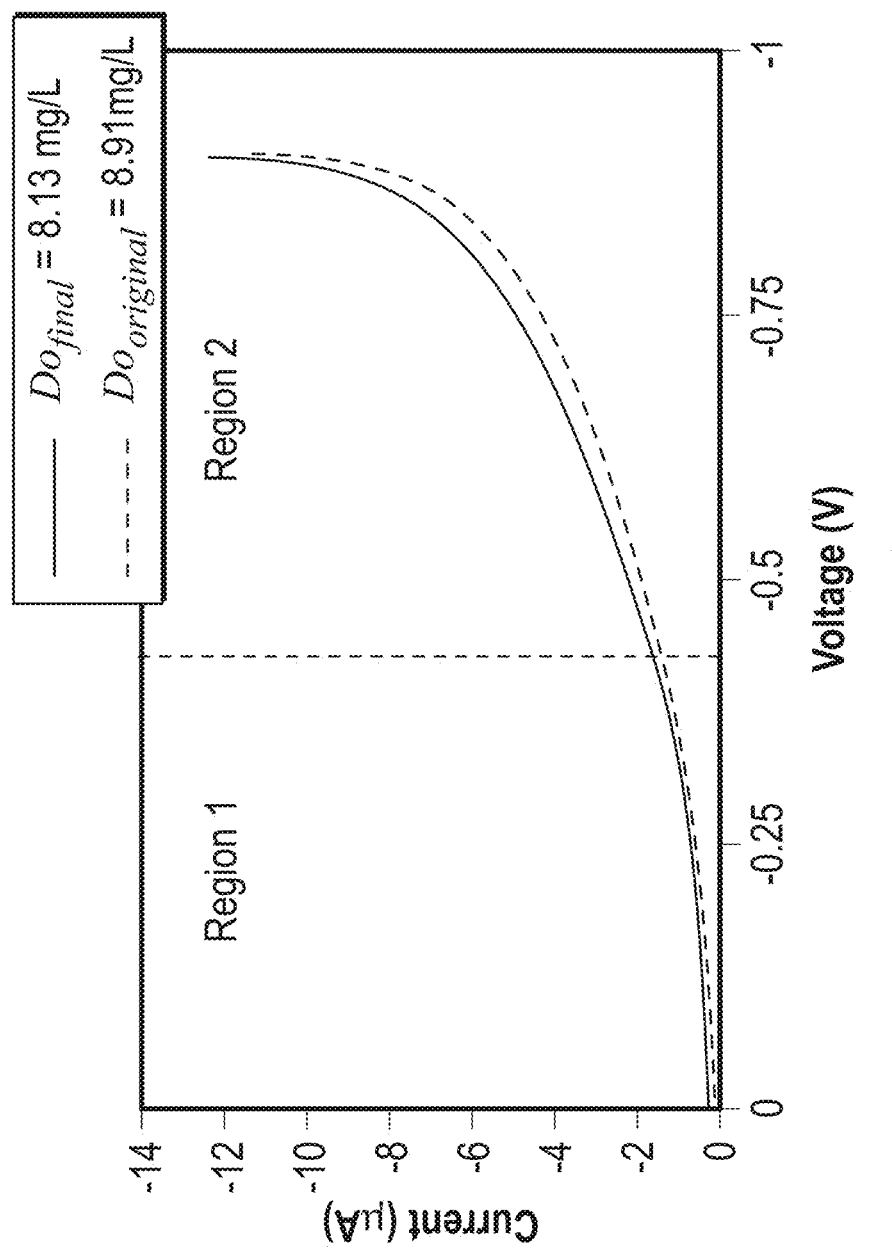
FIG. 15C shows the response of exemplary MEA sensors and commercial probes to the shock of DO.

In addition, similar to the temperature MEA, the potential-time program was recorded every 0.1 seconds or less (FIG. 15B), and thus capturing the current change simultaneously under the shock. The shock pattern measured by the conductivity MEA exhibited three stages: stable stage (before the shock), increase stage (during the shock) and decrease stage (after the shock) (FIG. 15B). The conductivity instantaneously increased after the shock injection, and the maximum conductivity (256.9 µS/cm) was even higher than the final conductivity value (FIG. 15B) due to the rapid diffusion of the shock solution into the original solution. Afterwards, the conductivity value of the mixed solution gradually dropped and stabilized to the final conductivity (190.8 µS/cm), which fit into the theoretical value of the mixed solution (185 µS/cm). These transient changes of the conductivity shock were not captured by the commercial conductivity probe that could only record the steady increase of conductivity to the final value (FIG. 15B).

d. Sensitivity and Accuracy of MEAs Under Shocks of DO and pH in Water Solutions For the DO shock (FIG. 15C), the original solution had the DO concentration of 8.91 mg/L, and the shock solution had the DO of 0.2 mg/L. The DO concentration of the final mixed solution was about 8.13±0.26 mg/L and verified by the commercial DO sensor. Because the DO MEA monitored the DO concentration by acquiring different reduction currents in cyclic voltammetry (CV) programs, it took a long duration period (around 2 minutes) and could not capture the transient shock details as commercial DO probes. Previous study found that modifying the DO working electrode with platinum nanoparticles could allow the usage of the reduction current-time program for obtaining datasets, which was expected to shorten the data acquisition time and enable recording more details of DO shock. The ratio of the estimated DO (based on the DO MEA model) to the actual DO concentrations (based on the reading of the commercial DO probe) ranged between 98.50% and 101.50%, demonstrating that the superb accuracy of the DO MEA (>100±1.50%).

Figure 15D:
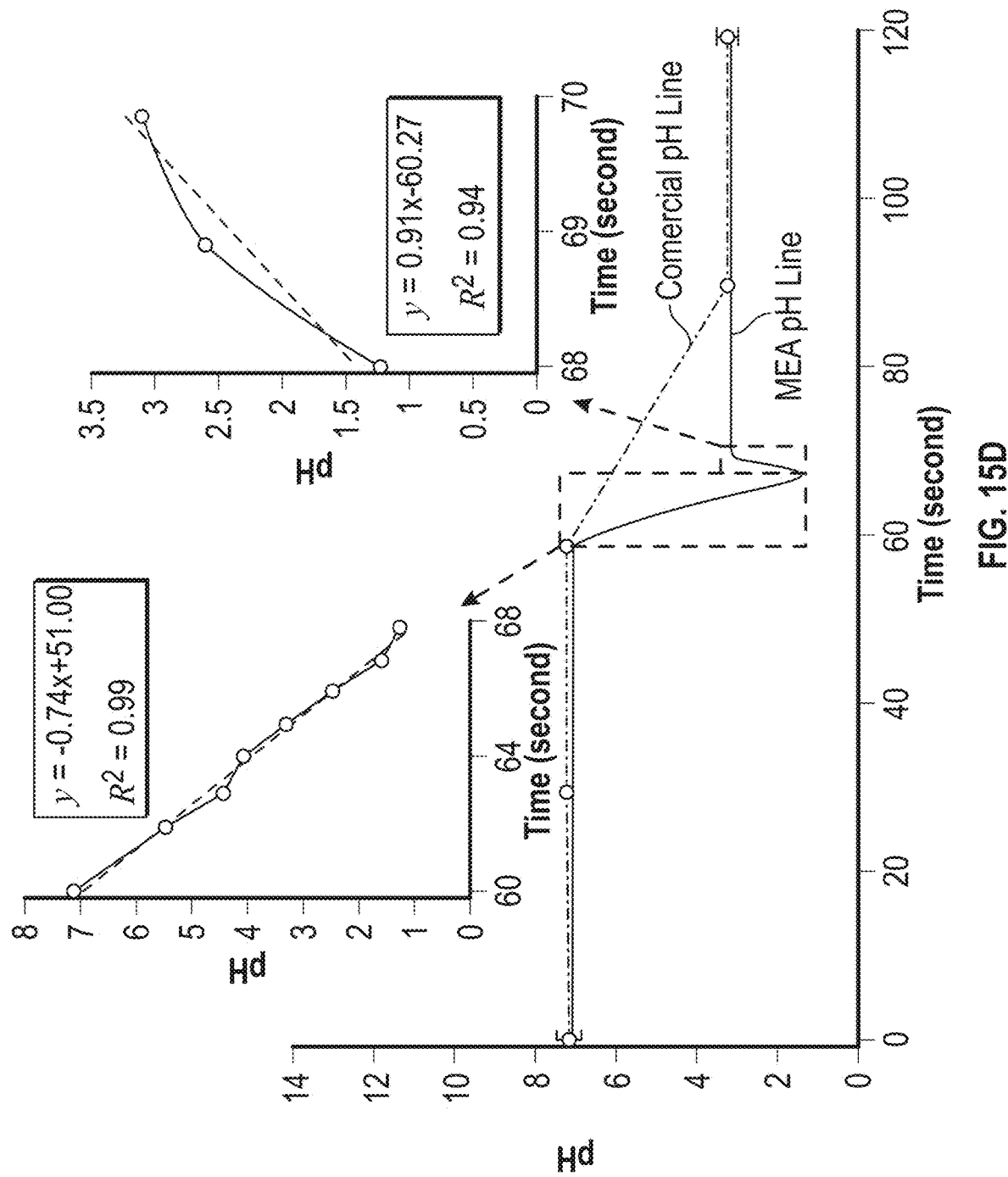
FIG. 15D shows the response of exemplary MEA sensors and commercial probes to the shock of pH.

For the pH shock (FIG. 15D), the original solution (DI water at 20° C.) had the pH of 7.08, and the shock solution had the pH of 2.09. Based on the conservation of electric charge and the volume ratio, the final mixed solution had the pH of 3.04, which was verified by the commercial pH probe (pH reading: 3.06). The ratio of the estimated pH (based on the pH MEA model) to the actual pH (based on the pH commercial probe) ranged between 98.50% and 101.50%, demonstrating the superb accuracy of the pH MEA sensor (>100±1.50%). The pH shock profile of the pH MEA showed that pH instantaneously dropped after the pH shock injection, and the bottom point (pH: 1.24) of the pH profile was even lower than the final pH value due to the rapid diffusion of the shock solution into the original solution. Then the pH value of the mixed solution gradually increased and stabilized to the final pH (pH: 3.06), which fit the theoretical value of the mixing final pH (pH: 3.05). These transient changes of the pH shock were not captured by the commercial pH probe that could only record the steady decrease of pH to the final value. Because the pH MEA recorded the open potential every 0.1 second and the mm-sized pH MEA was much smaller than the commercial pH sensor (~8-10 mm), the pH MEA sensors exhibited high accuracy and fast response time.

e. Long-Term Stability Test of MEA Sensors to the Wastewater and the Wasted Sludge The stability of MEA sensor is critical for long-term wastewater monitoring.

Electrode fouling caused by the attachment of inorganic/organic particles has been well known to cause the deterioration of sensor accuracy and stability. The MEA surfaces did not have obvious change based on macroscopic and microscopic observation during 4-week immersion in wastewater and waste sludge. The resistance of the temperature MEA slightly increased with the time, since the trace biofilms reduced the surface area of the MEA. However, the low slope (1.226) of the regression indicated that the resistance of the temperature MEA only decreased less than 0.1% in one week, demonstrating the high stability of the MEA. Furthermore, the accuracy of the MEAs (temperature, conductivity, DO and pH) had no obvious change within the 4-week operational period, with the reading accuracy of 100%±1.25% (max. ±2.0%) compared with commercial probes. There were three main reasons for the good stability of MEA sensors. First, the whole MEA entity except electrodes in the working electrode was coated with the waterproof layer (poly ink/sealant silicone), which prevented the attachment of inorganic/organic particles on the electrode layer directly. Second, the smooth surface of the substrate (Kapton film) prevented the attachment of inorganic/organic particles. Third, gold and silver nanoparticles printed on the mm-sized electrodes had been found to have high anti-fouling capability.

f. Significance of MEA Profiling in Water/Wastewater Treatment

Water quality monitoring is critical to reveal the operational status and provide high quality dataset for system control and adjustment in water and wastewater treatment processes. Existing expensive yet inefficient "single-point" probes and "multi-parameter" meters can only monitor parameters at single point without obtaining the complete picture of system status. This study aimed at renovating water quality monitoring technology by patterning multiple types of mm-sized electrodes on a single flexible film using IPT. MEA sensors achieved real-time in situ multiple-parameter monitoring in a single measurement, and provided a complete dataset of system physic-chemical and biochemical status. MEA sensors exhibited high accuracy, excellent signal stability, rapid response time and long-term robustness, which pose a great potential to detect the fluctuant water quality in treatment processes. The IPT fabrication possesses three major breakthroughs over traditional PCVD: facile fabrication condition, flexible MEA film structure and low fabrication cost, which makes the installation of multiple MEAs possible to ensure high resolution sensing of complex infrastructure, and execute swift and proactive decision-making strategy. The batch tests in real wastewater and waste sludge clearly showed the high stability of MEA sensors. Future study will be conducted in continuous flow wastewater systems to validate the anti-fouling capability of MEA sensors.

As shown herein, advantageous micro-electrode arrays (MEA) fabricated using IPT according to the present disclosure may be effectively employed in water quality sensing applications. By printing multiple mm-sized electrodes on a single flexible film, the MEA possessed distinct advantages over traditional "single-point" probes: small sensor size, compact structure, multiple-parameter measurement in a sampling, easy fabrication and deployment, long-term stability, and ultralow low cost. Four types of MEA sensors (temperature, conductivity, DO and pH) showed high accuracy in the calibration tests, and fast response time and excellent sensitivity in the shock tests. MEA sensors revealed more transient details than commercial probes, and achieved the auto-correction. Four-week tests in wastewater and waste sludge showed MEA surface was still intact and exhibited a high stability for long-term applications. The study clearly demonstrates that MEA technology will enable the heterogeneous profiling with a simple easy configuration, and provide high resolution sensing of complicated water/wastewater treatment infrastructure.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

The invention claimed is:

1. A method for utilizing a sensor assembly comprising:
providing a substrate, the substrate having a length and a width, and a plurality of micro-electrodes deposited on the substrate, wherein the plurality of micro-electrodes includes micro-electrodes adapted to detect (i) physical parameters of temperature and conductivity, and (ii) chemical parameters of oxygen concentration and pH, wherein (a) the plurality of micro-electrodes are laid out in a plurality of rows to define a micro-electrode matrix, (b) each of the plurality of rows includes micro-electrodes adapted to detect the physical parameters of temperature and conductivity, and micro-electrodes adapted to detect the chemical parameters of oxygen concentration and pH, and (c) each of the micro-electrodes includes a printed electrode element and a waterproof coating that covers the printed electrode element, but leaves uncovered measurement electrode portions;
disposing the substrate at least partially within and along the depth of a water treatment system so as to expose the plurality of micro-electrode rows to varying water depths within the water treatment system;
operating the plurality of micro-electrodes to simultaneously detect physical parameters of temperature and conductivity, and chemical parameters of oxygen concentration and pH at varying depths of the water treatment system.

2. The method of claim 1, wherein the substrate is a flexible plastic film.

3. The method of claim 1, wherein each micro-electrode of the plurality of micro-electrodes includes gold or silver.

4. The method of claim 1, wherein the water treatment system is selected from the group consisting of aeration tanks, anaerobic digestors, anoxic tanks, storage tanks, pipelines, sedimentation tanks, sludge tanks, chlorination tanks, watershed sites and sediment restoration sites.

5. The method of claim 1, wherein the plurality of micro-electrodes includes from about 48 to about 500 micro-electrodes deposited on the substrate.

6. The method of claim 1, wherein the plurality of micro-electrodes further comprises at least one micro-electrode that can be adapted to detect a parameter selected from the group consisting of redox potential parameters, ammonium parameters, metal ion parameters, pesticide parameters, salt parameters and nutrient parameters.

7. The method of claim 1, wherein each micro-electrode of the plurality of micro-electrodes has a length of about 5 mm and a width of about 5 mm on the substrate.

8. The method of claim 1, wherein depositing the plurality of micro-electrodes on the substrate includes inkjet printing the plurality of micro-electrodes on the substrate.

9. The method of claim 1, wherein the substrate includes multiple different parameter detecting micro-electrodes aligned in multiple horizontal and vertical rows along the length and width of the substrate.

* * * * *